US005672717A

United States Patent [19]
Verkade et al.

[11] Patent Number: 5,672,717
[45] Date of Patent: Sep. 30, 1997

[54] PREPARATION OF PYRROL AND OXAZOLE COMPOUNDS; FORMATION OF PORPHYRINS AND C-ACYL-α-AMINO ACID ESTERS THEREFROM

[75] Inventors: John Verkade, Ames, Iowa; Jianseng Tang, Lisle, Ill.

[73] Assignee: Iowa State University Research Foundation, Inc., Ames, Iowa

[21] Appl. No.: 691,002

[22] Filed: Nov. 22, 1995

Related U.S. Application Data

[63] Continuation-in-part of Ser. No. 441,958, May 16, 1995, Pat. No. 5,554,764, which is a continuation of Ser. No. 291,409, Aug. 16, 1994, Pat. No. 5,446,166, which is a division of Ser. No. 142,775, Oct. 26, 1993, Pat. No. 5,367,084.

[51] Int. Cl.$^6$ ................................................. C07D 403/14
[52] U.S. Cl. ........................................... 548/518; 548/519
[58] Field of Search ..................................... 548/518, 519

[56] References Cited

U.S. PATENT DOCUMENTS

| | | | |
|---|---|---|---|
| 3,987,128 | 10/1976 | Richman | 260/936 |
| 4,840,935 | 6/1989 | Wagnon et al. | 514/18 |
| 5,051,533 | 9/1991 | Verkade | 564/13 |
| 5,260,436 | 11/1993 | Verkade et al. | 544/193 |
| 5,367,084 | 11/1994 | Verkade et al. | 548/518 |
| 5,446,166 | 8/1995 | Verkade et al. | 548/236 |

FOREIGN PATENT DOCUMENTS

| | | |
|---|---|---|
| 0 315 931 | 7/1989 | European Pat. Off. |
| 63-238078 | 10/1988 | Japan |

OTHER PUBLICATIONS

Ellis et al. Chem Abstracts, 117:92626u (1992).

Y. Aoyama et al., "5,15-Bis(8-Quinolyl)- and -Bis(2-Pyridyl)Octaethylporphyrin. Preparation, Stabilities of Atropisomers, and Metal-ion Binding Properties", *Tetrahedron Lett.*, 28, 2143-2146 (1987).

Y. Aoyama et al., "Molecular Recognition in the Ternary Systems of a Trifunctional Chiral Metalloporphyrin, Amino Esters, and HPLC Adsorbent", *Tetrahedron Lett.*, 29, 5271-5274 (1988).

Y. Aoyama et al., "Binding of Amino Acids with a Bifunctional Metalloporphyrin via Concurrent Metal-Coordination and Electrostatic Interactions", *Chemistry Letters*, 1877-1880 (1989).

D.H.R. Barton et al., "A New Synthesis of Pyrroles from Nitroalkenes", *J. Chem. Soc., Chem. Commun.*, 1098-1100 (1985)

D.H.R. Barton et al., "A new synthesis of pyrroles from nitro alkenes", C. A., (104: 109403a), 703, (1986).

D.H.R. Barton et al., "A Useful Synthesis of Pyrroles from Nitroolefins", *Tetrahedron Lett.*, 46, 7587-7598 (1990).

C.K. Chang et al., "A Convenient Synthesis of Pyrrole Precursors for Octaalkylporphyrins", *Synthesis*, (Jul. 1979), 548-549.

D.O. Cheng et al., "Synthesis of Substituted Porphyrins", *Tetrahedron Lett.*, 17, 1469-1472 (1977).

J.P. Chupp et al., "Heterocycles from substituted amides. VII. Oxazoles from 2-isocyanoacetamides", *8-Heterocycles*, (94: 47193w), 567 (1981).

P.S. Clezy et al., "Chemistry of Pyrrolic Compounds", *Aust. J. Chem.*, 11, 1835-1845 (1965).

* E. Glatstein et al., "Photodynamic Therapy: Shining Light Where it is Needed", *J. Clin. Oncology*, 11, 1844-1845 (Oct. 1993).

M.J. Gunter et al., "Synthesis and Atropisomer Separation of Porphyrins Containing Functionalization at the 5,15-Meso Positions: Application to the Synthesis of Binuclear Ligand Systems", *J. Org. Chem.*, 46, 4792-4795 (1981).

M. Miyoshi et al., "5-Substituted oxazole-4-carboxylates", *C. A. (28235t)*, 83, 512 (1975).

Y. Murakami et al., "Transition-Metal Complexes of Pyrrole Pigments. XV. Coordination of Pyridine Bases to the Axial Sites of Cobalt Corroles", *Bull. Chem Soc. Jpn.*, 51, 123-129 (1978).

A.I. Myer, Ed., "3,4-Diethylpyrrole and 2,3,7,8,12,13,17,18-Octaethylporphyrin", *Organic Synthesis*, 70, 67-77 (1991).

H. Ogoshi et al., "Synthesis of 5-Aryl- and 5,15-Diaryl-2,3,7,8,12,13,17,18-Octaethylporphines", *Chemistry Letters*, 29-32 (1978).

H. Ogoshi et al., "Novel Chiral Porphyrins with $C_2$ Symmetry", *Tetrahedron Lett.*, 27, 6365-6368 (1986).

H. Ogoshi et al., "Selective Synthesis of Unsymmetrical Meso-Arylporphyrins", *Tetrahedron Lett.*, 32, 4529-4532 (1991).

N. Ono et al., "Synthesis of Octaalkyl- and Octaarylporphyrins from Nitroalkenes", *Chemistry Letters*, 1511-1514 (1988).

N. Ono et al., "Preparation of Pyrroles Having Long Alkyl Chains from Nitroalkenes", *Bull. Chem. Soc. Jpn.*, 61, 4470-4472 (1988).

(List continued on next page.)

*Primary Examiner*—Joseph McKane
*Attorney, Agent, or Firm*—Merchant, Gould, Smith, Edell, Welter & Schmidt, P.A.

[57] ABSTRACT

A process for preparation of new or previously known pyrrol derivatives is provided. The process involves reacting a nitroalkane or a nitroalkene with an isocyanoacetate in the presence of a prophosphatrane "super base" to prepare the pyrrol compounds. Through production of new pyrrol compounds, new pyrrol derivatives such as dipyrromethanes and porphyrins may be synthesized. In addition, the high yields of pyrrol compounds produced according to the method of the invention provide for more efficient production of previously known dipyrromethane and porphyrin compounds. The invention further provides a mild, high yield process for de-esterification of esterified pyrrol and dipyrromethane compounds. The invention also provides a synthetic method for the production of high yields of oxazoles through reaction of an aryl halide or acid anhydride with an isocyanoacetate in the presence of a prophosphatrane "super base". The product oxazoles serve as intermediates for subsequent treatment to provide pharmaceutically interesting C-acyl-α-amino acid esters.

1 Claim, No Drawings

OTHER PUBLICATIONS

N. Ono et al., "A Convenient Synthesis of Trifluoromethylated Pyrroles and Porphyins", Bull. Chem. Soc. Jpn., 62, 3386–3388 (1989).

N. Ono et al., "Porphyrin Synthesis from Nitrocompounds", Tetrahedron, 46, 7483–7496 (1990).

Y. Ozaki et al., "Syntheses of 5-substituted oxazole-4-carboxylic acid derivaties with inhibitory activity on blood platelet aggregation", C. A., (100: 120941n), 582 (1984).

J.B. Paine III et al., "Pyrrole Chemistry. The Cyanovinyl Aldehyde Protecting Groups", J. Org. Chem., 41, 2826–2835 (1976).

J.B. Paine, III et al., "An Improved Synthesis of Octaethylporphyrin", J. Org. Chem., 41, 3857–3860 (1976).

R. Rusch et al., "New 21,22-Dioxaporphyrin-5(23H)-one, Oxygen Analogs of Oxophlorins", Liebigs Ann. Chem., 1187–1158 (1990).

A.S. Semeikin et al., "Study of Conditions for Condensation of Pyrrol with Aldehydes into Porphyrise", Izv. Vyss. Uchelon. Zared Khim. Technol., 31, 39–44 (1988).

M. Suzuki et al., "Convenient Synthesis of Aroylamino Acids and A–Amino Ketones", Syn. Commun., 2, 237–242 (1972).

M. Suzuki et al., "Synthesis of amino acids and related compounds. 6. New convenient synthesis of a–C–acylamino acids and a–amino ketones", C. A. (137467h), 79, 414 (1973).

M. Suzuki et al., "New Convenient Synthesis of A–C–Acylamino Acids and A–Amino Ketones", J. Org. Chem. 38 3571–3575 (1973).

* H. Toi et al., "Paramagnetic $^{19}$F N.M.R. Spectra of Iron(III) Porphyrins Substituted with $CF_3$ Groups and Reconstituted Myoglobin", J. Chem. Soc., Chem. Commun., 24, 1791–1792 (Dec. 1985).

J.G. Verkade et al., "The Unusually Robust P–H Bond in the Novel Cation HP $(NM_eCH_2CH_2)_3N$", J. Am. Chem. Soc., 111, 3478 (1989).

J.G. Verkade et al., "An Improved Synthesis of the Strong Base $P(MeNCH_2CH_2)_3N$", Tetrahedron Lett., 34 2903–2904 (1993).

J.G. Verkade et al., "$[P(MeNCH_2CH_2)_3N]$ as a Superior Catalyst for the Conversion of Isocyanates to Isocyanurates", Angew. Chem. Int. Ed. Engl., 32, 896–898, (1993).

J.G. Verkade et al., "Chemical and Structural Implications of Bond Formation Between the Bridgehead Atoms in $Z-P(MeNCH_2CH_2)_3N$ Systems", Phosphorus, Sulfur, and Silicon, 75, 205–208, (1993).

R.W. Wagner et al., "An Improved Synthsis of Tetramesitypoprhyrin", Tetrahedron Lett., 28, 3069–3070 (1987).

H.W. Whitlock et al., "Octaethylporphyrin", J. Org. Chem., 33, 2169–2171 (1968).

R. Young et al., "Synthesis and Characterization of Blocked and Ligand–Appended Hemes Derived from Atropisomeric Meso–Diphenylporphyrins", J. Am. Chem. Soc., 107, 898–909 (1985).

PREPARATION OF PYRROL AND OXAZOLE COMPOUNDS; FORMATION OF PORPHYRINS AND C-ACYL-α-AMINO ACID ESTERS THEREFROM

CROSS-REFERENCE TO RELATED APPLICATIONS

This is a continuation-in-part of U.S. patent application Ser. No. 08/441,958, now U.S. Pat. No. 5,554,764, filed May 16, 1995. U.S. Ser. No. 08/441,958 is a continuing application of U.S. Ser. No. 08/291,409, now U.S. Pat. No. 5,446,166 filed Aug. 16, 1994, which is a divisional of U.S. Ser. No. 08/142,775, now U.S. Pat. No. 5,367,034, filed Oct. 26, 1993.

GOVERNMENT SUPPORT

This invention was made with government support funded by the Department of Commerce under Grant ITA-87-02 and by the National Science Foundation under Grant No. CHE-8908136. The government has certain rights in the invention.

FIELD OF THE INVENTION

The present invention is directed in part to methods for the preparation of new or previously known pyrrol, dipyrromethane and porphyrin compounds. The invention specifically provides synthetic methods for the production of pyrrol derivatives. The invention further describes newly discovered porphyrin compounds, as well as methods to produce these or previously known porphyrin compounds. The invention is also directed to synthetic methods for production of oxazoles, which may, for example, serve as intermediates for subsequent treatment to provide C-acyl-α-amino acid esters.

BACKGROUND OF THE INVENTION

Certain pyrrol derivatives are known to be important intermediates in the synthesis of bioactive porphyrins such as octaethylporphyrin. For example, pyrrol derivatives, compounds A–C, and the dipyrromethanes D and E have been utilized as intermediates in the synthesis of octaethylporphyrin (compound F where $R^1=R^2=Et$) and for the preparation of certain fluoro substituted porphyrins (e.g. compound G where $R^1=R^2=Et$, $R=C_6H_4-CF_3$). The former is widely used for biological modeling studies and the latter porphyrins are potential agents for the treatment and diagnosis of cancers. Pyrrol derivatives are also important intermediates for synthesizing biopigments, drugs and agrochemicals.

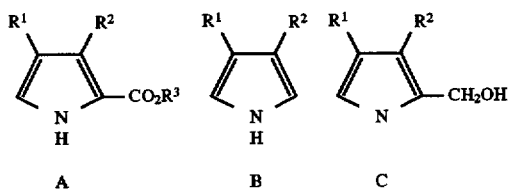

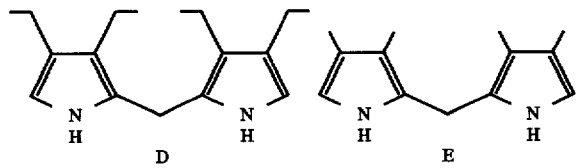

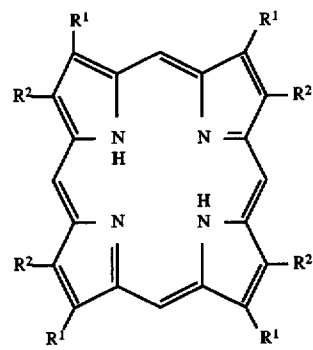

F

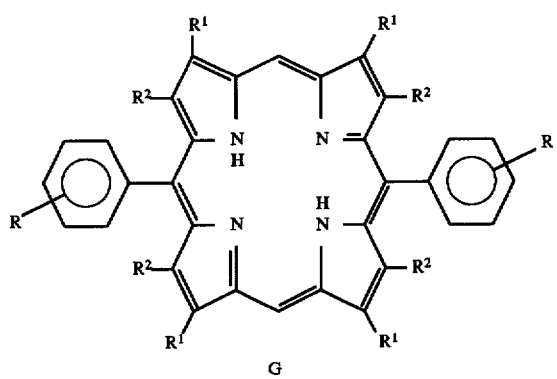

G

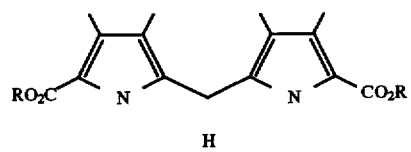

H

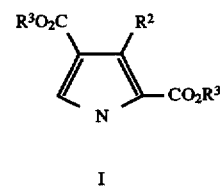

I

Previously reported synthetic methodologies for pyrrol derivatives are often tedious, and typically provide relatively low yields. For example, 3,4-diethylpyrrol (compound B where $R^1=R^2=Et$), has been prepared in the presence of 1,8-diazabicyclo[5.4.0]undec-7-ene (DBU), tetrahydrofuran (THF), and isopropylalcohol (IPA) in a relatively low yield (38.1–40%), Meyers, A. I., ED., 70 *Organic Synthesis*, 67–77 (1991). (Scheme 1)

Scheme 1

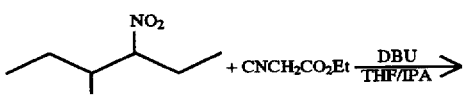

-continued
Scheme 1

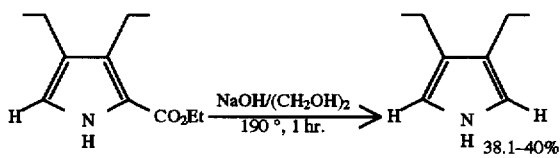

Tetrasubstituted dipyrromethanes are precursors for important types of sterically blocked meso-diarylporphyrins. Several have been prepared using lengthy procedures which provide low yields. (See e.g. Gunter, M. J. et al., *J. Org. Chem.*, 46:4792 (1981); Young, R. et al., *J. Am. Chem. Soc.*, 107:898 (1985)). For example, compound E (3,4,3',4'-tetramethyldipyrromethane) is a precursor for meso-diphenylporphyfin. Compound E has been prepared using involved methodologies which provide low yields (8–12%). (See e.g. Scheme 2.) Gunter et al., *J. Org. Chem.*, 46:4792 (1981); Young et al., *J. Am. Chem. Soc.*, 107:898 (1985).

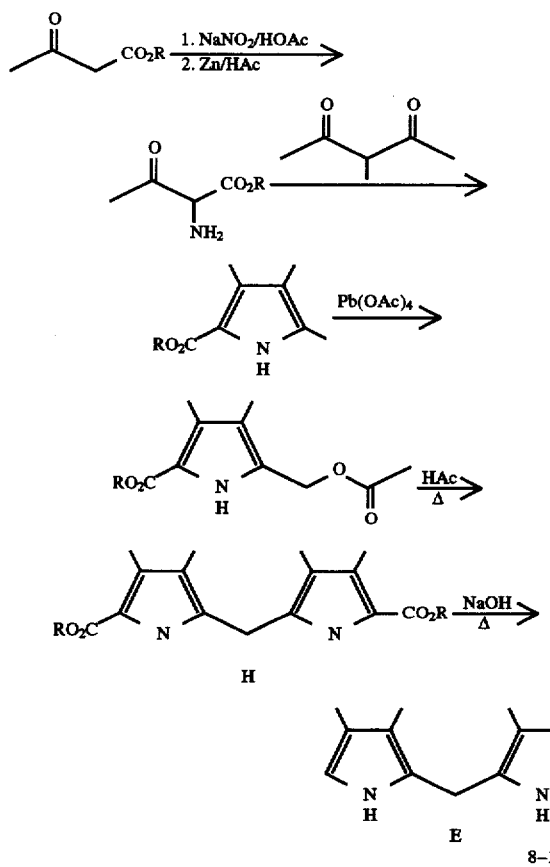

The Gunter et al., supra., and the Young et al., supra, method for the preparation of 3,3',4,4'-tetramethyldipyrromethane, and 3,3'-diethyl-4,4'-dimethyldipyrromethane involved the lengthy Knorr approach (ten or more steps) and gave a very low yield (≦10%). In particular, the decarboxylation of compound H with sodium hydroxide proceeds in very low yields owing to its decomposition at the elevated temperatures needed for decarboxylation (over 100° C.). A more recent revised procedure is also lengthy and of low yield (about 22%). See Scheme 3. Semeikin, A. S. et al., *Izv. Vyss. Uchelon. Zared Khim. Tekhnol.*, 31:39 (1988).

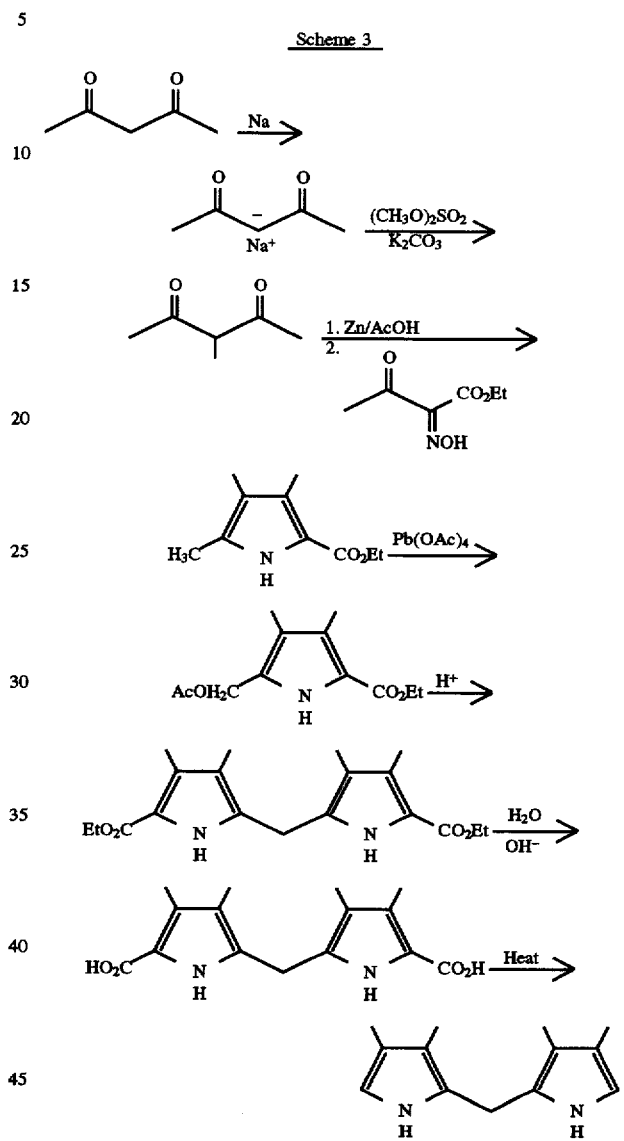

Irrespective of the route to the final product dipyrrol in Scheme 3, a frequent intermediate contains an ester group (—CO₂R group) at the alpha or 2 position. Removal of this ester group to form the de-esterified derivative has traditionally been problematic. Typically, an initial step for this process involves the common organic transformation of cleavage of the ester group to form a carboxylic acid by an acidic or basic hydrolysis. However, because pyrrol and dipyrromethane compounds are sensitive to acidic conditions, a more cumbersome procedure has been used to remove the alpha ester group of these compounds through the use of saponification and subsequent thermal decarboxylation. While this method provides a means of preparing 3,4-dialkylpyrrols such as compound B from an esterified compound such as compound A, the yield is very low (38–40%) and the product is not pure, thus requiring purification by vacuum distillation. (Scheme 1 .) Meyers, A. I., supra at 68.

The synthesis of porphyrins from pyrrol and dipyrromethane compounds, while well-known, has been of limited utility due to limited availability of pyrrol and dipyrromethane starting compounds. Most of the methods for the synthesis of octaethylporphyrin (OEP) start from 2-ethoxycarbonyl-3,4-diethyl-5-methylpyrrol, which was prepared by the Knorr reaction of ethyl propionylacetate with 2,4-pentanedione. Pain, III, J. B., et al., *J. Org. Chem.*, 44:3857 (1976). (Scheme 2.) This method is inconvenient because of difficulties in preparing the starting materials and in transforming the 5-methyl group of the pyrrol ring system. Although new methods have been designed prior to the techniques disclosed herein, the preparation of OEP has remained troublesome, particularly whenever more than a few grams are required. This is so because of the accompanying formation of by-product I which lowers the yield of the desired pyrrol compound A, and allows it to be isolated only on a small scale by a difficult chromatography procedure. Ono, N., et al., *Tetrahedron*, 46:7843 (1990).

Oxazoles (compound J) are intermediates to pharmaceutically interesting C-acyl-α-amino acids (compound K) which, in turn, are useful intermediates in the synthesis of β-hydroxyamino acids, especially β-aryl sefines and amino alcohols including sympathomimetic agents such as ephedrine and epinephrine.

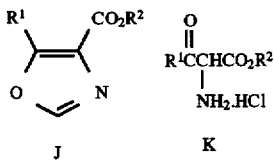

Traditional synthesis of oxazoles through reaction of isocyanoacetates with acyl chlorides or acid anhydrides in the presence of a large excess of 1,8-diazabicyclo[5.4.0]undec-7-ene (DBU) or triethyl amine are typically lengthy (about 48 hours). M. Suzuki et al., *Syn. Commun.*, 2:237–242 (1972); Suzuki et al., *J. Org. Chem.*, 38:3571 (1973). Modifying the traditional method of oxazole synthesis by reacting an acyl halide with an isocyanoacetate in tetrahydrofuran (THF) in the presence of only 1 equivalent DBU (Scheme 4), and shortening the reaction time to two hours while stirring at room temperature, produced a mixture with a complicated ¹H NMR spectrum, and a GC pattern, which showed that based on the limiting starting reactant, only about eight percent of the desired oxazole was formed.

Scheme 4

SUMMARY OF THE INVENTION

The invention provides a method for preparation of new or previously known pyrrol derivatives including pyrrol, dipyrromethane and porphyrin compounds. The invention further provides a method for preparation of oxazoles which may serve as intermediates for the pharmaceutically interesting C-acyl-α-amino acids which, in turn, are useful intermediates in the synthesis of β-hydroxy amino acids.

According to the method of the invention, pyrrol compounds may be produced by reacting an isocyanoacetate compound with a prophosphatrane base and a nitro alkane compound of general formula $(H)(Z)(R^2)C\text{—}C(NO_2)(R^1)$ (H) or a nitroalkene according to the formula $(H)(R^2)C\text{=}C(NO_2)(R^1)$ wherein $R^1$ and $R^2$ are substituents which are nonreactive under conditions of the reaction and Z is a leaving group under the conditions of the reaction.

Herein when it is said that a group R (for example $R^1$ or $R^2$) is non-reactive under the reaction conditions it is meant that the group R is such that it does not participate in the reaction and it does not undergo chemical change or transformation during the reaction.

The R groups $R^1$ and $R^2$ should also be such that they do not prevent the reaction. Herein when it is said that an R group (for example $R^1$ and $R^2$) should be chosen such that it does not "prevent" reaction, it is meant that the group is selected such that the reactants can react in the manner described; for example, the R groups do not provide sufficient steric hinderance for non-reactivity, nor do they prevent sufficient solubility for reaction.

Herein guidance with respect to "non-reactive" R groups and R groups that do not "prevent" reaction is provided in each instance by representative groups. It is not meant, however, that the lists are exclusive.

Although not wishing to be held to any particular theory, it is speculated that the prophosphatrane base of general structure

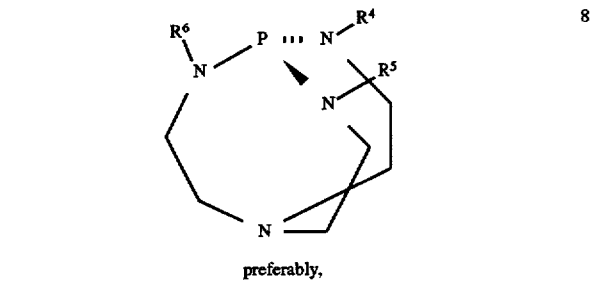

preferably,

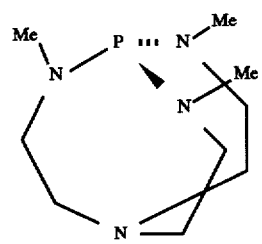

causes deprotonation of the isocyanoacetate compound to yield an isocyanoacetate anion which then condenses with the nitroalkane or nitroalkene compound to form a pyrrol derivative of general structure

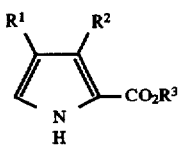

The reaction is preferably conducted in an organic non-protic solvent with or without the presence of isopropyl alcohol. The reaction may be conducted over a temperature range of about −30° to 60° C., preferably below 0° C. and typically takes about one and one-half to four hours for completion.

The product pyrrol compound 1 bearing an ester group (i.e., a —CO₂R group) at a position alpha to the ring nitrogen may be decarboxylated through the use of a lithium halide in a polar aprotic solvent. Unlike prior methods for removal of a carboxy ester from pyrrol derivatives, the method of the invention provides a high yield of the de-esterified product in a simple one-pot reaction without the need for saponification and subsequent thermal decarboxylation.

The method of the invention further provides a process for producing pyrrol derivatives such as dipyrromethanes from esterified pyrrol compounds. Herein the term "esterified pyrrol compound" is meant to refer to a material having an ester group (—CO₂R) substituted on a pyrrol ring. If the estefified pyrrol compound starting materials are produced according to the method of the invention, isolation from the reaction mixture is not necessary. The esterified pyrrol compounds are reacted with an acid catalyst and an aldehyde or aldehyde precursor to form the dipyrromethane products. The pyrrol ester compound used as a starting reagent to make the dipyrromethane products will yield a diesterified dipyrromethane product. The ester groups may be removed from the dipyrromethane products through the use of lithium halide in a polar aprotic solvent as previously described for the pyrrol ester compounds. The process of the invention provides for new dipyrromethane and diesterified dipyrromethane products.

The pyrrol compounds, produced according to the method of the invention, may be further reacted, with or without isolation from the reaction mixture, to produce porphyrin products. Because the invention provides a method for producing new pyrrol compounds and dipyrromethane, use of such compounds as building blocks to form porphyrins provides a means for production of new porphyrin products. In addition, the invention provides for a high-yield process for formation of asymmetrical porphyrins through the use of dipyrromethane compound starting materials which may be produced from pyrrol compounds according to the method of the invention.

The prophosphatrane base is also useful, according to the method of the invention, to prepare oxazole compounds of the general structure:

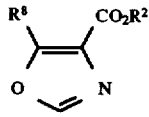

According to the method of the invention, an acyl halide or an acid anhydride compound is reacted with the prophosphatrane base in the presence of an isocyanoacetate to yield the product oxazole. The reaction is conducted in a suitable organic non-protic solvent. The product oxazole may be further utilized to prepare C-acyl-α-amino acid esters by reacting the oxazole product with an acid and an alcohol.

All products of the invention are produced under relatively mild conditions in high yields.

DETAILED DESCRIPTION OF THE INVENTION

The methods described herein provide for the synthesis of relatively pure pyrrol derivatives in high yields. The disclosure provides for the synthesis of new pyrrol compounds which may serve as intermediates for pyrrol derivatives such as dipyrromethane compounds and pharmacologically important porphyrin products. Through the synthesis of new pyrrol compounds, the disclosure also provides for the synthesis of new porphyrin compounds. The invention also provides a new and mild method for removal of ester groups from pyrrol and dipyrromethane compounds without the cumbersome use of saponification and subsequent thermal decarboxylation steps. In addition, the disclosure provides a new and efficient method of producing relatively pure oxazole compounds in high yields which may be used as intermediates in the formation of C-acyl-α-amino acid esters.

I. Preparation of Pyrrol Compounds

The present invention provides for the efficient preparation of pyrrol derivatives, including pyrrol compounds 1–3, dipyrromethane compounds 4 and 5, and porphyrin compounds 6 and 7.

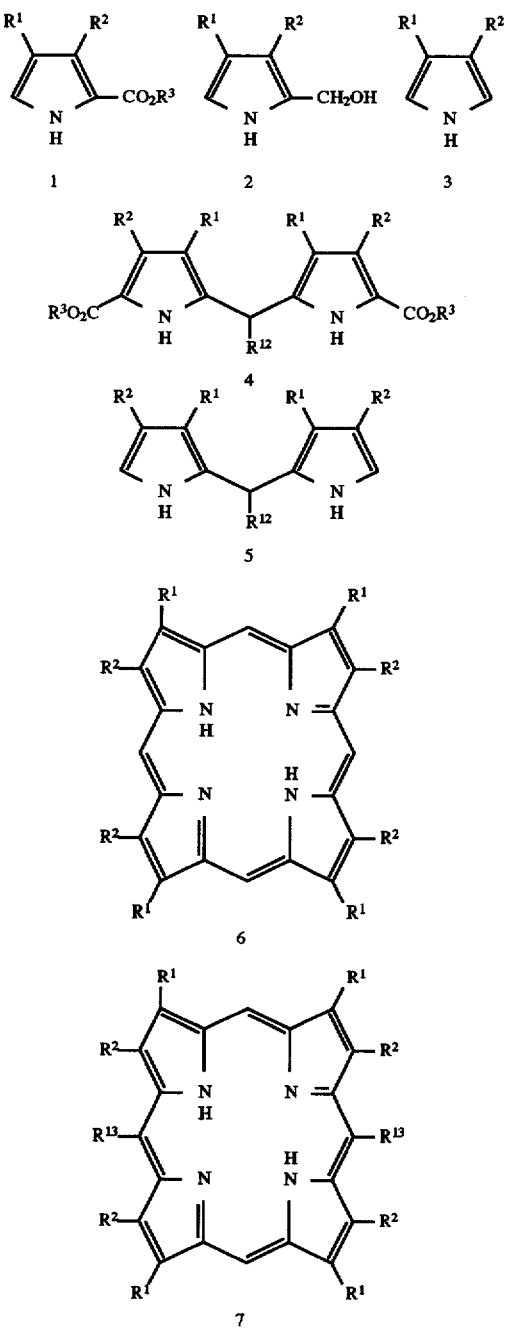

According to the present invention, a general, flexible reaction scheme usable to generate selected pyrrol derivatives is provided and reflected in Scheme A, as follows:

Scheme A

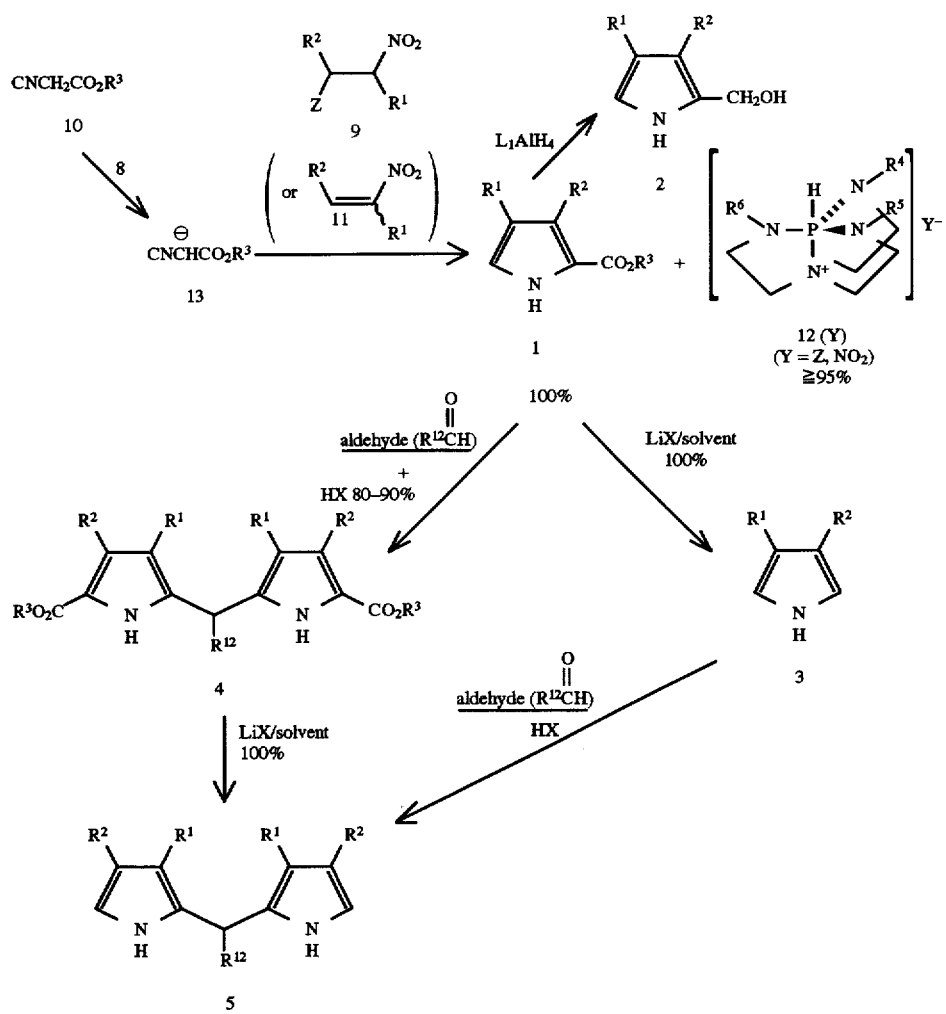

The method of the invention provides for reacting a nitroalkane compound, substituted with a suitable leaving group, or a nitroalkene compound, with an isocyanoacetate compound in the presence of a strong base to produce a pyrrol compound. Herein the term "nitroalkane compound", compound 10, is meant to refer to a compound according to the formula $(H)(Z)(R^2)C-C(NO_2)(R^1)(H)$; and the term "nitroalkene compound", compound 11, is meant to refer to a compound according to the formula $(H)(R^2)C=C(NO_2)(R^1)$. According to the method of the invention, the nitroalkane compound is preferably substituted at the carbon alpha to the $-NO_2$ bearing carbon with an electronegative group which acts as a leaving group (i.e., it is according to the formula $(H)(Z)(R^2)C-C(NO_2)(R^1)(H)$ wherein the electronegative group is represented by (Z)). Suitable leaving groups include OAc, Br, Cl, triflate, tosylate and mesylate. $R^1$ and $R^2$ are substituents as described below. A preferred embodiment, as shown in general Scheme A, involves the reaction of a nitroalkane (compound 9) wherein group Z is an acetoxy group ($-OAc$), or a nitroalkene (compound 11) with an isocyanoacetate (compound 10) in the presence of a strong non-ionic base, in a polar aprotic solvent to produce the pyrrol ester compound 1.

Herein the term "ester group" is meant to refer to a group according to the general formula ($-CO_2R^3$). The term "pyrrol ester compound" is meant to refer to a compound which includes a pyrrol ring substituted with an ester group, regardless of other substituents in the compound. Herein, the term "de-esterification" in the context of a pyrrol ester is meant to refer to removal of a $-CO_2R^3$ group from the pyrrol ester compound. The reaction generates the pyrrol derivative (compound 1) in relatively high yield (greater than 80%, typically at least 98% based on a molar equivalent mount of the limiting reactant of compound 9, 10, and 11). The product pyrrol compound may be further reacted to produce dipyrromethane and porphyrin compounds. The subsequent de-esterification of compounds 1 and 4 to yield compounds 3 and 5, respectively, is described in detail in Section IB.

According to the method of the invention, the strong base reacted with the nitroalkane or nitroalkene compound is preferably a non-ionic prophosphatrane base according to the general formula (compound 8):

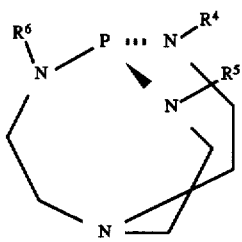

also sometimes referred to as "superbase."

It is understood that each methylene (that is each $CH_2$ group in each —$CH_2CH_2$-group situated between two N atoms) depicted in compound 8 bears two hydrogen atoms, which may each be independently substituted with up to two R groups which do not inhibit the reaction in the formation of the pyrrol compound. R groups which may be independently substituted for a methylene hydrogen include, for example, alkyl, substituted alkyl, aryl, and substituted aryl. Addition of R groups may produce steriogenic carbon centers leading to chirality of 8 which may influence the course of reactions with chiral substrates. As an example of a chiral form of 8, consider the structure below which is chiral and can also exist as its enantiomer.

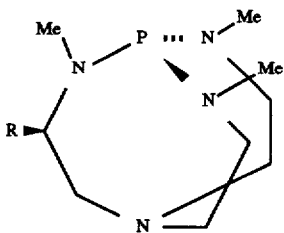

A preferred base, according to the method of the invention, is trimethyltriazaprophosphatrane (P(MeNCH$_2$CH$_2$)$_3$N), (compound 8a).

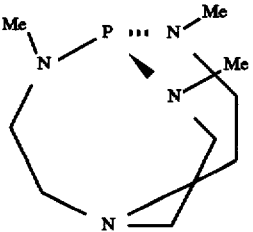

Synthesis of preferred bases according to the present invention is generally described in U.S. Pat. No. 5,051,533, the disclosure of which is incorporated herein by reference. An improved and preferred base is also described in Verkade, J. G. et al., *J. Am. Chem. Soc.* 111:3478 (1989). An improved and preferred synthesis of base 8a is described in Verkade et at., *Tetrahedron Lett.*, 34:2903 (1993). The base, compound 8a, is commercially available from Strem Chemical Company (Newbury Port, Mass.).

Although no specific mechanism is asserted, it is believed that the strong basicity of the non-ionic base, compound 8, makes the complete reaction of a substituted nitroalkane or a nitroalkene with an isocyanoacetate compound to yield a pyrrol compound very fast (typically less than 2 hours) under mild conditions (for example, room temperature). It is believed that the base, compound 8, deprotenates the isocyanoacetate (compound 10) to produce a form of isocyanoacetate anion (compound 13). If a substituted nitroalkane (compound 9) is used as a reactant, it is believed that the base (compound 8) will also cause conversion of compound 9 to the nitroalkene (compound 11) by deprotonation and loss of the leaving group (Z). Once formed, the isocyanoacetate anion (compound 13) condenses with the nitroalkene (compound 11) to produce the pyrrol ester compound 1. Because it is not necessary to isolate compound 1 prior to further reaction, the one-pot reaction procedure is efficient and desirable.

The superbase (compound 8) has good solubility in solvents which are nonpolar (for example, benzene and hexane) and polar (for example, THF, diethyl ether, ethylacetate, acetonitrile and pyridine). The corresponding protonated prophosphatrane, compound 12(Y), wherein Y=NO$_2$, OAc, Cl, Br, or I, is insoluble in nonpolar and weakly polar solvents such as benzene, hexane, THF and diethyl ether but is very soluble in water. (It is noted that the anion Y will comprise both the NO$_2$ group from the nitroalkane or nitroalkene, and the leaving group of the nitroalkane compound.) The product pyrrol, compound 1, is very soluble in nonpolar solvents such as hexane and benzene, weakly polar solvents such as ether and THF, and some polar solvents such as ethylacetate and acetone. The large difference in solubility between product 1 and compound 12(Y), allows product 1 to be isolated in high yield by filtration of 12(Y). The salt of base 8, namely compound 12(Y), can subsequently be deprotonated with t-BuOK, in high yield, allowing the base, compound 8, to be recycled. This provides additional economy for the procedure.

From the general procedure outlined in Scheme A, it will be understood that a variety of 3,4-disubstituted 2-ester pyrrols, according to the general formula of compound 1, can be prepared. It is foreseen that preferred compounds in which R$^1$=R$^2$=Et will be synthesized as intermediates for unique symmetrical and unsymmetrical porphyrin syntheses, as outlined below.

A. Preparation of Pyrrol Derivative 1

According to the method of the invention, pyrrol derivatives, 1, may be prepared in greater than about 80%, preferably greater than 90%, and typically greater than 98% yield (based on the molar equivalent amount of the most limiting starting reactant). The method provides for about a one molar equivalent of starting nitroalkene (compound 11), about one equivalent of isoeyanoacetate (compound 10) and at least about one equivalent superbase 8 (preferably 8a) to form a near molar equivalent of pyrrol compound 1. If the starting nitro compound is a nitroalkane (compound 9), at least about two molar equivalents of the superbase (compound 8, preferably compound 8a) must be added to one molar equivalent of isocyanoacetate and one molar equivalent nitroalkane to form a single molar equivalent of pyrrol product. The additional molar equivalent of superbase is necessary to effect complete conversion of the nitroalkane (compound 9) to the nitroalkene (compound 11) as well as to deprotonate the isocyanoacetate. It is understood that the reaction will provide high product yields in the presence of some excess base.

The starting nitroalkane, (compound 9), is substituted at the position alpha to the carbon with the NO$_2$ thereon, with a leaving group (Z). This leaving group is electronegative and may be selected from known leaving groups such as OAc, Br, Cl, triflate, tosylate and mesylate groups. In a preferred embodiment, the leaving group is OAc. Alternatively a nitroalkene (compound 11) starting material which lacks a leaving group may be used.

The nitroalkane (compound 9) or nitroalkene (compound 11) are shown substituted at the nitro-bearing carbon and at the alpha carbon with R groups designated as R$^1$ and R$^2$, respectively. The stereochemistry of R$^1$ at the double bond of the nitroalkene may be either the cis or trans configuration. A wavy line in the diagrammatic schemes represents that the $R^1$ may be cis or trans. According to the method of the invention $R^1$ and $R^2$ may be any group that is nonreactive under conditions of the reaction. In this context, it is understood that with respect to any given group $R^n$ (wherein $R^n$ is any R group used according to the invention), the term "nonreactive" means that the R group does not undergo a chemical change, reaction or transformation during the reaction(s) of concern. Also, preferably the R groups are such that they do not prevent the formation of the desired reaction product. $R^1$ and $R^2$ suitable for the method of the invention include substituted and unsubstituted alkyls, cycloalkyls, alkenyls, and aryls. All alkyls and alkenyls may be branched or straight chain. Throughout the present disclosure "Me" refers to a methyl ($-CH_3$) group and "Et" refers to an ethyl ($-CH_2CH_3$) group. Although not exhaustive, $R^1$ and $R^2$ may be independently selected from the group including H, $C_1$–$C_{20}$ alkyl, $C_1$–$C_{20}$ cycloalkyl, $C_1$–$C_{20}$ alkenyl, benzyl, $C_5$–$C_{20}$ aryl, F, Cl, Br, I, $NO_2$, $NH_2$, $SO_3H$, OH, OMe, OEt; substituted $C_1$–$C_{20}$ alkyl, $C_1$–$C_{20}$ cycloalkyl, $C_1$–$C_{20}$ alkenyl, benzyl, $C_1$–$C_{10}$ aryl, wherein the substitution includes one or more $C_1$–$C_{20}$ alkyl, F, Cl, Br, I, OMe, OEt, Me, $CF_3$, $NO_2$, $NH_2$, $SO_3H$, OH groups; or $R^1$ and $R^2$ may also be referred to collectively as an $-R^1R^2-$ group wherein they are joined as part of a $C_4$ or larger C—C ring system, C—C ring size being limited by steric or solubility effects, preferably $-R^1R^2-$ is a substituted or unsubstituted $C_2$–$C_8$ carbon bridge forming a $C_4$–$C_{10}$ ring. Substitutions on the carbons of the carbon bridge are those which are non-reactive according to the method of the reaction, preferred carbon bridge substitutions include one or more $C_1$–$C_{20}$ alkyl, F, Cl, Br, I, OMe, OEt, Me, $CF_3$, $NO_2$, $NH_2$ groups. $R^3$ of the isocyanoacetate (compound 10) starting material is selected from any group which is nonreactive under the conditions of the reaction mixture. $R^3$ may be selected from the group including alkyls and benzyls, including unsubstituted $C_1$–$C_4$ alkyl and benzyl; $C_1$–$C_4$ alkyl and benzyl substituted at any carbon with one or more substituents selected from the group consisting essentially of $C_1$–$C_4$ alkyl, F, Cl, Br, I, OMe, OEt, $NO_2$ and $NH_2$.

The reaction is generally conducted in a suitable solvent. Solvents which are suitable for the reaction generally include organic non-protic solvents. Suitable solvents include THF, 1,4-dioxane, $CH_3CN$, dimethylformamide (DMF), diethyl ether and mixtures of these materials. The reaction may be conducted with or without the presence of isopropyl alcohol, which is presently believed to act as a temporary proton donor. The reactants may be combined with the solvent in any order. Preferably the superbase is added to the mixture to cause deprotonation of compound 10 before addition of compound 11. If the starting nitro compound is the nitroalkane 9, the base may be added to a mixture of compound 9 and 10.

The reaction mixture is stirred until completion of the reaction. The reaction may be conducted over a temperature range of about –30° to 60° C., but it is preferably conducted below 0° C. Formation of compound 1 from starting reactants occurs within 8 hours, typically 1.5 to 4 hours. Completion can be determined by $^{31}P$ and $^1H$ NMR spectroscopy.

The reaction procedure of the invention allows for synthesis of pyrrol compounds which can immediately be utilized as starting materials for the synthesis of pyrrol derivatives such as dipyrromethanes or porphyrin compounds without further purification. Pyrrol products may also be isolated by chromatography or recrystallization. The isolated pyrrol derivatives are stable and may be stored at about 25° C. or below.

The starting materials, 9 and 11, are very easily prepared in high yield as described in Barton, D. H. R. et al., *Tetrahedron*, 46:7587 (1990); Ono, N. et at., *Tetrahedron*, 46:7483 (1990); and Ono, N. et al., *Bull. Chem. Soc. Japan*, 61:4470 (1988), which are incorporated by reference herein. Compound 10 is commercially available from Aldrich Chemical Company (Milwaukee, Wis). $R^1$ and $R^2$ in compound 9 and 11 can be various groups, as previously described, which are thus introduced at the 3,4 and/or 3',4' positions, respectively, in the pyrrol ring(s) of 1, 2, 3, 4, and 5. One merit of the synthesis of 5 ($R^1=R^2=Et$) is that the biological application and usefulness of the corresponding new meso-porphyrins from this compound will be greatly enhanced because the ethyl side chains on the rings will render the meso-porphyrins soluble in organic solvents.

As stated earlier, although no mechanism is asserted, it is believed that the strong basicity of 8 allows the rapid and complete conversion of 9 to 11 and 10 to 13. This is followed by condensation of 11 with the deprotonated isocyanoacetate anion, 13, even at low temperatures. Anion 13 obtained in this manner appears to be more nucleophilic by comparison with similar anions deprotonated by ionic bases or weak non-ionic bases such as DBU and guanadines. Barton, D. H. R., et al., *Tetrahedron*, 46:7587 (1990); Ono, N., et at., *Bull. Chem. Soc. Japan*, 61:4470 (1988). Thus, the stronger basicity of 8 resulting in the enhanced nucleophilicity of 13 allows the reaction to proceed at –20° to –15° C. to afford compound 1 as the only pyrrol product. In comparison, the use of the weaker base DBU gives almost no product 1 at lower temperature (–20° to –15° C.), although at room temperature the reaction occurs slowly to give both 1 and the by-product 16 (see Scheme B). The latter compound, 16, is believed to be formed by a side reaction of 13 and 15 which is facilitated by the higher temperature decomposition of 14.

Scheme B

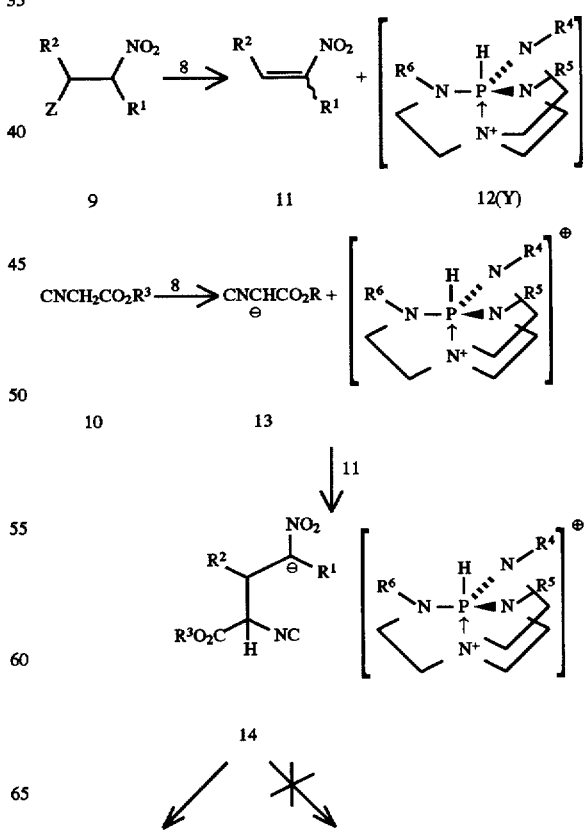

-continued
Scheme B

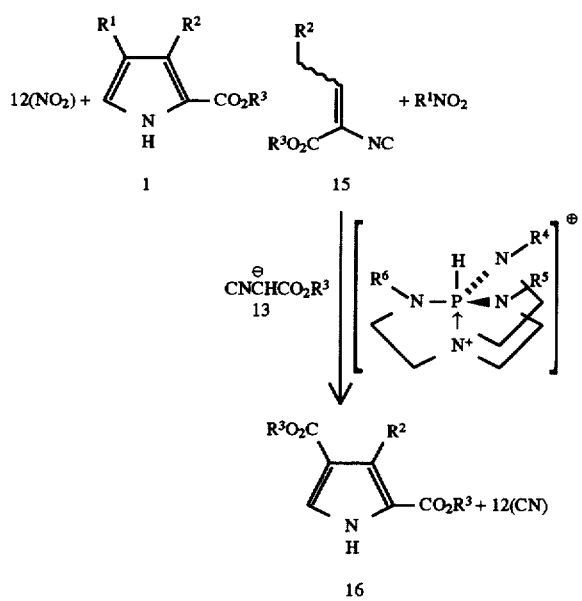

Because it is not necessary to isolate compound I when conducted as a one-pot reaction procedure, the present method provides a substantial savings in labor and cost compared with the Knorr approach. It is also advantageous to use 8, preferably 8a, rather than DBU or other weak bases because of the higher product yield, no detectable byproduct 16, and avoidance, if desired, of chromatographic isolation. As discussed earlier, the salt 12(Y) can be subsequently deprotonated in high yield with t-BuOK allowing 8 to be recycled, thus making the procedure even more economical.

B. Preparation of Pyrrol Compound 3

Methods of preparing de-esterified, 3,4-disubstituted pyrrols from compounds of the general formula of compound 1 are known. The cleavage of esters to yield a carboxylic acid, as a preliminary step to de-esterification, is a common organic transformation usually carried out in a routine manner by acidic or basic hydrolysis. However, pyrrol derivatives are sensitive to acidic conditions. Typically, removal of the alpha ester group from such sensitive materials, has been conducted by saponification and subsequent thermal decarboxylation. The yields for such de-esterification processes are generally low (38–40%) and the products have not been pure. Meyers supra. (See Scheme 1). According to the present invention, a new method is provided for removing the alpha ester group (—$CO_2R^3$) from pyrrol derivatives.

The pyrrol alpha ester derivatives of general structure of compound 1, derived as described in the foregoing discussion in Section IA, (whether or not isolated from the reaction mixture) may be de-esterified according to the method described in this Section of the invention. Alternatively, the pyrrol alpha ester compounds derived as described in Section IA, may first be reacted as described in Section II to produce tetrasubstituted dipyrromethane diesters 4, and if desired these product dipyrromethanes may subsequently be de-esterified as described according to this Section of the invention. In general, esterified pyrrol derivatives of any source may be de-esterified according to the following method.

According to the method of the invention, pyrrol compounds of the general structure of compound 3 may be prepared in greater than about 80%, preferably greater than 90%, and typically greater than 98% yield based on a molar equivalent of compound 1 starting material. The method provides for mixing of pyrrol compound 1 with an excess of a lithium halide in a high boiling polar aprotic solvent to produce pyrrol compound 3. By "high boiling" in this context it is meant that the solvent has a boiling point of at least the temperature necessary to cause decomposition of the carboxylate group. Preferably, the solvent has a boiling point of 170°–250° C. Although no specific mechanism is asserted, it is believed that the mechanism generally involves an $S_N2$ substitution on the $R^3$ group of the ester by the halide of the lithium halide and subsequent thermal decarboxylation of the resulting carboxylate.

The starting pyrrol compound 1 may be substituted at the $R^1$, $R^2$ and $R^3$ positions. The invention provides for substitution of any group at $R^1$, $R^2$ and $R^3$ which is not reactive under the conditions of the reaction. Also, preferably $R^1$, $R^2$ and $R^3$ are such that they do not prevent formation of the desired pyrrol derivatives under the reaction conditions. $R^1$ and $R^2$ may comprise substituted and unsubstituted alkyls, cycloalkyls, alkenyls and aryls, and $R^3$ may comprise alkyls and benzyls. The alkyls and alkenyls may be branched or straight chain.

The solvents suitable for the method of the invention are high boiling polar aprotic solvents such that the solvents boil at a temperature high enough to cause decomposition of the carboxylate group. High-boiling polar aprotic solvents suitable for the method of the invention include dimethyl sulfoxide (DMSO), dimethylformamide (DMF), 1,3-dimethyl-α-imidozoline and 2,4,6-collidine. It is understood that the lithium halide suitable for the method of the invention includes all lithium halide compounds.

In a preferred embodiment, a pyrrol compound of the general structure of compound 1 wherein $R^1$ and $R^2$ may be independently selected from the non-exhaustive group including H, $C_1$–$C_{20}$ alkyl, $C_1$–$C_{20}$ cycloalkyl, $C_1$–$C_{20}$ alkenyl, benzyl, $C_5$–$C_{20}$ aryl, F, Cl, Br, I, $NO_2$, $NH_2$, $SO_3H$, OH, OMe, OEt; substituted $C_1$–$C_{20}$ alkyl, $C_2$–$C_{20}$ cycloalkyl, $C_1$–$C_{20}$ alkenyl, benzyl, $C_5$–$C_{20}$ aryl, wherein the substitution includes one or more $C_1$–$C_{20}$ alkyl, F, Cl, Br, I, OMe, OEt, Me, $CF_3$, $NO_2$, $NH_2$, $SO_3H$, OH groups and $R^1$ and $R^2$ may also be referred to as —$R^1R^2$— wherein they are joined as part of a $C_4$ or larger C—C ring system, C—C ring size being limited only by steric or solubility effects, preferably —$R^1R^2$— is a substituted or unsubstituted $C_2$–$C_8$ carbon bridge forming a $C_4$–$C_{10}$ ring. Substitutions on the carbons of the carbon bridge are those which are non-reactive according to the method of the reaction, preferred carbon bridge substitutions include one or more $C_1$–$C_{20}$ alkyl, F, Cl, Br, I, OMe, OEt, Me, $CF_3$, $NO_2$, $NH_2$ groups. $R^3$ includes unsubstituted $C_1$–$C_4$ alkyl and benzyl; $C_1$–$C_4$ alkyl and benzyl substituted at any carbon with one or more substituents selected from the group consisting essentially of $C_1$–$C_4$ alkyl, F, Cl, Br, I, OMe, OEt, Me, $CF_3$ $NO_2$ or $NH_2$ is reacted with 15–150 molar equivalents of a lithium halide in the order of preference, LiCl>LiBr>LiI, in a solvent such as DMSO. The reaction mixture is stirred and heated to reflux, typically about 180°–250° C. Completion can be determined by TLC or any other suitable method. The reaction will usually be complete within 6 hours, typically within 1.5 hours. The reaction rate for lithium halides decreases in the order: LiCl (typically 1.5 hours), LiBr (typically 2.0 h), and LiI (typically 3.0 h) for production of compound 3.

Advantages of the present method are: (1) $S_N2$ dealkylation with LiX in a typical solvent such as DMSO is very fast and complete in 1.5 to 3.0 hours at reflux; (2) the decarboxylation produces pyrrol in high yield in a one-pot reaction; (3) the product is formed quantitatively and no further purification is generally necessary; (4) the dealkylation and subsequent decarboxylation process can be carried out on a large scale; and (5) the $S_N2$ dealkylation reaction is highly selective for an ester of an unhindered alcohol, preferably methyl and ethyl esters, so advantage can be taken of selectivity in developing more complicated reaction schemes. In general, the alpha-lithium carboxylate intermediate is quickly decarboxylated to 3,4-disubstituted pyrrol without isolation, in contrast to the traditional saponification and subsequent decarboxylation technique which gives less than a 40% yield in 6–12 hours.

II. Preparation of Dipyrromethane Compounds

A further embodiment of the present disclosure is a method for synthesizing 3,3',4,4' tetrasubstituted dipyrromethanes in a simple two-step process which typically gives 80–90% yield based on 1 (Scheme A). Indeed, new dipyrromethane compounds can be obtained by using new pyrrol compound starting materials produced according to the method of the invention described in Section I. The dipyrromethanes can be further utilized in an improved method for the synthesis of certain porphyrins, for example, asymmetrical porphyrins. The method of the invention may be used for synthesis of meso-diarylporphyrins (compound 7).

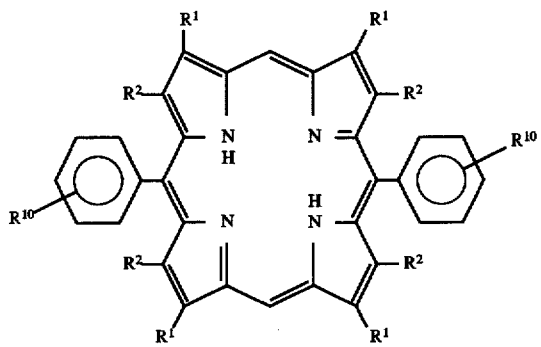

As discussed earlier, Gunter et al. supra and Young et al. supra have reported this porphyrin system, which appears to be attractive for biological purposes in that the ortho-substituted conformational isomers, which are difficult to interconvert (atropisomers), can be separately obtained, and each isomer may be manipulated further to yield a variety of useful model heme compounds. This useful porphyrin system, however, has not been widely exploited. This is at least in part attributable to the difficulty in obtaining the dipyrromethane intermediates. As noted before, the prior methods to synthesize dipyrromethanes involve lengthy processes with low yields. (See Scheme 3.)

The following new method utilizes esterified 3,4-disubstituted pyrrols (compound 1) as starting substrates to form the pyrrol derivative 2,2'-diester 3,3',4,4,' tetrasubstituted dipyrromethane (compound 4). 2,2'-diester-3,3',4,4,' tetrasubstituted dipyrromethane products may subsequently be de-esterified, by the method of the invention described in Section IB, to yield 3,3',4,4,4,' tetrasubstituted dipyrromethane (compound 5). See Scheme A.

According to the method of the invention, a pyrrol derivative of the general structure of compound 1 is condensed with an aldehyde or an aldehyde precursor in the presence of a catalyst, which is a strong acid soluble in an organic solvent, to produce the desired dipyrromethane products, compounds 4 and 5 of Scheme A. The inventors recognize that ketones, or other compounds having a reactive carbonyl carbon, may be substituted for aldehydes to the extent that substituents at the carbonyl carbon do not cause significant inhibition of dipyrromethane formation under the conditions of the reaction. As used herein, an aldehyde refers to a compound of general formula $R^{12}$ CHO. $R^1$, $R^2$, $R^3$ and $R^{12}$ may be any group such that they are nonreactive according to the method of the reaction. Also, preferably $R^1$, $R^2$, $R^3$ and $R^{12}$ are such that they do not prevent formation of the desired dipyrromethane compounds under the conditions of the reactions. $R^1$ and $R^2$ may include substituted and unsubstituted alkyls, cycloalkyls, alkenyls, and aryls. The alkyls and alkenyls may be branched or straight chain. $R^3$ substitutions which are nonreactive according to the method of the reaction include alkyls and benzyls. The esterified pyrrol, compound 1, may be derived from the process described in Section I, or from other sources wherein preferred $R^1$ and $R^2$ may independently be H, $C_1$–$C_{20}$ alkyl, $C_1$–$C_{20}$ cycloalkyl, $C_1$–$C_{20}$ alkenyl, benzyl, $C_5$–$C_{20}$ aryl, F, Cl, Br, I, $NO_2$, $NH_2$, $SO_3H$, OH, OMe, OEt; substituted $C_1$–$C_{20}$ alkyl, $C_2$–$C_{20}$ cycloalkyl, $C_1$–$C_{20}$ alkenyl, benzyl, $C_5$–$C_{20}$ aryl, wherein the substitution is one or more $C_1$–$C_{20}$ alkyl, F Cl, Br, I, OMe, OEt, Me, $CF_3$, $NO_2$, $NH_2$, $SO_3H$, OH groups; and $R^1$ and $R^2$ may also be referred to as —$R^1R^2$— wherein they are joined as part of a $C_4$ or larger C—C ring system. C—C ring size being limited by steric or solubility effects, preferably —$R^1R^2$— is a substituted or unsubstituted $C_2$–$C_8$ carbon bridge forming a $C_4$–$C_{10}$ ring. Substitutions on the carbons of the carbon bridge are those which are nonreactive according to the method of the reaction, preferred carbon bridge substitutions include one or more $C_1$–$C_{20}$ alkyl, F, Cl, Br, I, OMe, OEt, Me, $CF_3$, $NO_2$, $NH_2$. $R^3$ includes unsubstituted $C_1$–$C_4$ alkyl and benzyl; $C_1$–$C_4$ alkyl and benzyl substituted at any carbon with one or more substituents selected from the group consisting essentially of $C_1$–$C_4$ alkyl, F, Cl, Br, I, OMe, OEt, Me, $CF_3$, $NO_2$ or $NH_2$.

Added to about one equivalent of compound 1 is about one to five equivalents of an aldehyde ($R^{12}$CHO or $(R^{12}CHO)_n$) or an aldehyde precursor such as dimethoxymethane in the presence of an acid catalyst such as HCl, HBr, PTSA, $BF_3.OEt_2$ or similar catalysts. According to the invention, $R^{12}$ may be selected from the non-exhaustive group including H, $C_1$–$C_{20}$ alkyl, $C_1$–$C_{20}$ alkenyl, $C_1$–$C_{20}$ cycloalkyl, benzyl, $C_5$–$C_{20}$ aryl; substituted $C_1$–$C_{20}$ alkyl, $C_1$–$C_{20}$ alkenyl, $C_2$–$C_{20}$ cycloalkyl, benzyl, $C_5$–$C_{20}$ aryl, wherein the substitution is one or more $C_1$–$C_{20}$ alkyl, F, Cl, Br, I, OMe, OEt, Me, $CF_3$, $NO_2$ or $NH_2$. Preferred $R^{12}$ substituents include, for example, H, $CF_3$, $CH_2CF_3$, $CF_2CH_3$, $CF_2CF_3$, $CF_3$ substituted phenyl (at the o, m, or p position) and phenyl substituted with one or more F groups. If desired, the product, compound 4, may be subsequently dealkyl(benzyl)ated using a lithium halide and subsequently decarboxylated in a high-yield one-pot reaction as described earlier in Section IB.

As previously discussed, the method of the invention in Section IA greatly expands the availability of novel pyrrol starting reagents. As a result, the number of tetrasubstituted dipyrromethane compounds capable of being produced is widely expanded. Examples of new dipyrromethanes, 4, synthesized according to the invention include, 4a ($R^1$=$R^2$=Et, $R^3$=Me $R^{12}$=H), 4b ($R^1$=Et, $R^2$=$CF_3$, $R^3$=Et $R^{12}$=H), 4c ($R^1$=Me, $R^2$=$CF_3$, $R^3$=Me, $R^{12}$=H), 4d ($R^1$=Et, $R^2$=$CF_3$, $R^3$=Me, $R^{12}$=H), 4e (—$R^1R^2$—=—$CH_2(CH_2)_2CH_2$—, $R^3$ =Me or Et $R^{12}$=H) and 4f ($R^1$=Et, $R^2$=Et, $R^3$=Me, $R^{12}$=p-$C_6H_4CF_3$). Additional compounds 4 which can be produced according to the invention include a compound wherein $R^1$ and $R^2$ are each independently $C_1$–$C_{20}$ alkyl, F, Cl, Br, I, $NO_2$, $NH_2$, $SO_3H$, OH, OMe; substituted $C_1$–$C_{20}$ alkyl, $C_1$–$C_{20}$ alkenyl, $C_2$–$C_{20}$ cycloalkyl, benzyl, $C_5$–$C_{20}$ aryl wherein the substitution is one or more $C_1$–$C_{20}$ alkyl, F, Cl, Br, I, OMe, OEt, $NO_2$, OH, $NH_2$, or $SO_3H$ groups; $R^3$=$C_1$–$C_4$ alkyl or a benzyl; and $R^{12}$=$CF_3$, $CH_2CF_3$, $CF_2CH_3$, $CF_2CF_3$, $CF_3$ substituted phenyl (at the o, m or p position) or a phenyl substituted with one or more F groups.

New de-esterified dipyrromethane product, 5, produced according to the method of the invention include 5a ($R^1$=Me, $R^2$=$CF_3$ $R^{12}$=H), 5b ($R^1$=Et, $R^2$=$CF_3$ $R^{12}$=H), and 5c ($R^1R^2$=—$CH_2(CH_2)_2CH_2$—, $R^{12}$=H). The yields of compounds 5a and 5b may be decreased due to sensitivity of the $CF_3$ group to lithium halides.

Other compounds of general structure 5 which can be produced according to the invention include compounds wherein $R^1$=Me or Et, $R^2$=$CF_3$ and $R^{12}$=H, $CF_3$, $CH_2CF_3$, $CF_2CH_3$, $CF_2CF_3$, $CF_3$ substituted phenyl (at the o, m or p position) or a phenyl substituted with one or more F groups; and $R^1$ and $R^2$ are linked to form a bridge —$R^1R^2$— wherein —$R^1R^2$— is —$CH_2(CH_2)_2CH_2$— and $R^{12}$=H, $CF_3$, $CH_2CF_3$, $CF_2CH_3$, $CF_2CF_3$, $CF_3$ substituted phenyl (at the o, m or p position) or a phenyl substituted with one or more F groups.

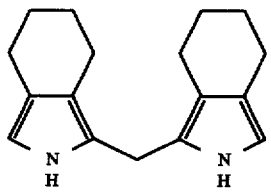

5c

III. Preparation of Porphyrins

According to the method of the invention, a further embodiment provides a method to produce known symmetrical porphyrins (Scheme C), for example octa-ethylporphyrin (OEP), in previously unobtainable yields. The method also provides for new asymmetrical porphyrins (Scheme D). The method utilizes a pyrrol derivative of general structure, compound 1, as a starting material for porphyrin synthesis. As a result, the greatly expanded number of new pyrrol compounds, 1, disclosed in Section IA, provides for synthesis of new porphyrin compounds in high yields. New asymmetrical fluorinated porphyrins prepared according to the method of the invention may be useful in the treatment of cancer (Scheme D). (See e.g., E. Glatstein et al.; *J. Clinical Oneology*, 11:1884 (October 1993); H. Toi et at., *J. Chem. Soc. Chem. Commun.*, :1791 (1985); JP 63,238,078; and EP 315,931.

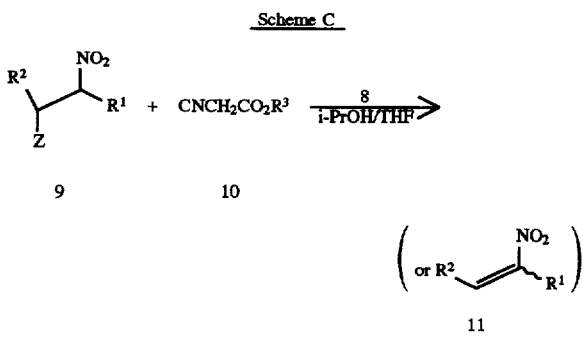

Scheme C

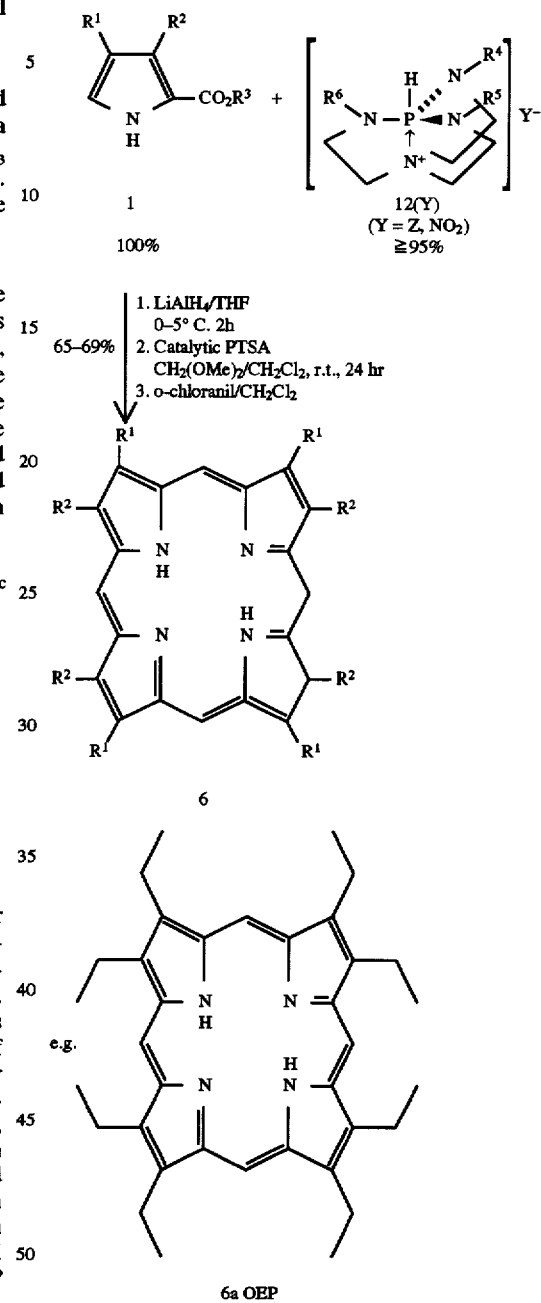

According to one embodiment of the invention, symmetrical porphyrins may be produced as follows: Pyrrol compounds of general structure of compound 1 are reduced at the ester to give a hydroxymethyl pyrrol compound, treated with a dehydrating agent in the presence of a catalyst and subsequently oxidized to produce the porphyrin product. The $R^1$, $R^2$, and $R^3$ substituents are selected such that they are nonreactive under conditions of the reaction. Also, preferably $R^1$, $R^2$ and $R^3$ are such that they do not prevent formation of the desired porphyrin compounds under conditions of the reaction. Preferred $R^1$ and $R^2$ substituents include alkyls, cycloalkyls, alkenyls, and aryls. Preferred $R^3$ substituents include alkyls and benzyls. $R^1$ and $R^2$ may be independently selected from the non-exhaustive group including H, $C_1$–$C_{20}$ alkyl, $C_1$–$C_{20}$ cycloalkyl, $C_1$–$C_{20}$ alkenyl, benzyl, $C_5$–$C_{20}$ aryl, F, Cl, Br, I, $NO_2$, $SO_3H$, OH, OMe, OEt; substituted $C_1$–$C_{20}$ alkyl, $C_1$–$C_{20}$ alkenyl, $C_1$–$C_{20}$ cycloalkyl, benzyl, $C_5$–$C_{20}$ aryl, wherein the substitution includes one or more $C_1$–$C_{20}$ alkyl, F, Cl, Br, I, OMe, OEt, Me, $CF_3$, $NO_2$, $NH_2$, $SO_3H$, OH groups; and $R^1$ and $R^2$ may also be referred to as —$R^1R^2$— wherein they are joined as part of a $C_4$ or larger C—C ring system. C—C ring size being limited by steric or solubility effects. Preferably —$R^1R^2$— is a substituted or unsubstituted $C_2$–$C_8$ carbon bridge forming a $C_4$–$C_{10}$ ring. Substitutions on the carbons of the carbon bridge are those which are non-reactive according to the method of the reaction, preferred carbon bridge substitutions include one or more $C_1$–$C_{20}$ alkyl, F, Cl, Br, I, OMe, OEt, Me, $CF_3$, $NO_2$, $NH_2$ groups. $R^3$ may be selected from the group including unsubstituted $C_1$–$C_4$ alkyl and benzyls; $C_1$–$C_4$ alkyl and benzyl substituted at any carbon with one or more substituents selected from the group consisting essentially of $C_1$–$C_4$ alkyl, F, Cl, Br, I, OMe, OEt, Me, $CF_3$, $NO_2$, or $NH_2$. The pyrrol compounds suitable as starting materials for this embodiment of the invention may be derived as described in Section IA or from any other source.

If the source of pyrrol compound 1 is the method as described in Section IA, the product pyrrol may be isolated prior to further reaction to form porphyrins, however isolation is not necessary for further reaction. Preferably, about one equivalent of compound 1 is added to a reducing agent such as a metal hydride, preferably $LiAlH_4$ in a suitable aprotic solvent, preferably a hydrocarbon or ether such as 1,4-dioxane, THF, $CH_3CN$, DME, or diethyl ether. The reaction mixture is stirred until completion at a temperature of about –20° to 20° C., preferably about –5° to 5° C. The reaction takes less than 6 hours to complete, typically about 2–3 hours. The product of the reaction is compound 2. Compound 2 is then added to an organic solvent for example, $CHCl_3$, $CH_3CN$, $CH_2Cl_2$ or benzene. To this mixture is added a strong acid, soluble in an organic solvent, in the presence of a dehydrating agent. Preferred strong acids which serve as an acid catalyst include PTSA, HBr, $BF_3.OEt_2$, and HCl. Suitable dehydrating agents include $CH_2(OMe)_2$ or $Me_2C(OMe)_2$. The mixture is stirred at 10°–30° C., preferably room temperature for about 24 hours. The product of the reaction is then oxidized with an oxidizing agent. Preferred oxidizing agents include $O_2$, 2,3-dichloro-5,6-dicyano-quinone, or o-chloranil in $CH_2Cl_2$. The oxidation typically takes about 24 hours at about 10°–30° C., preferably room temperature. Symmetrical porphyrins produced according to the method of the invention include, for example, 6b ($R^1R^2$=—($CH_2CH_2CH_2CH_2$)—):

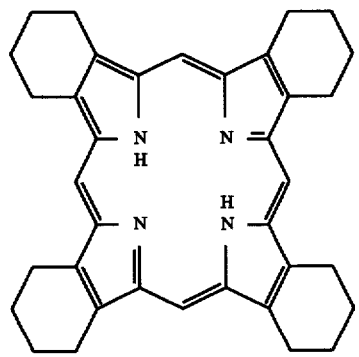

6b

Another embodiment of the present invention provides for the synthesis of porphyrins from dipyrromethane compounds, 5. The dipyrromethane compounds may be derived from pyrrol compounds as described in Section II or any other source. This method provides for formation of asymmetric porphyrins (Scheme D).

Scheme D

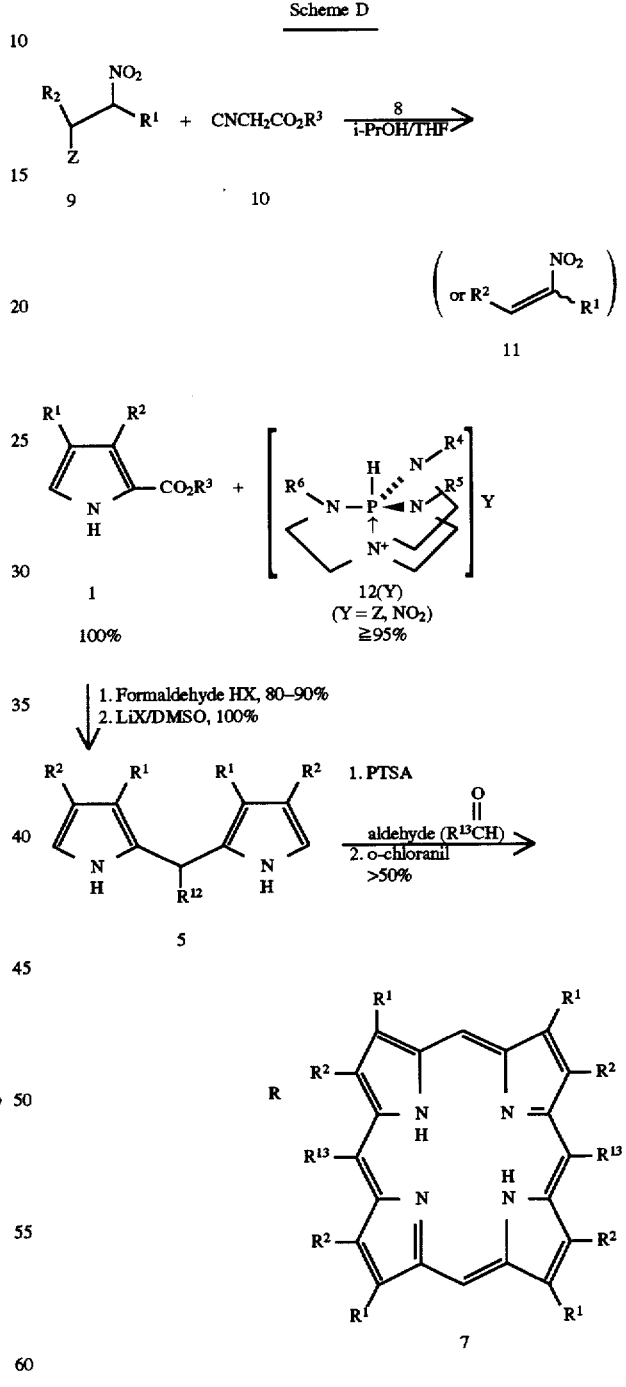

23
-continued
Scheme D

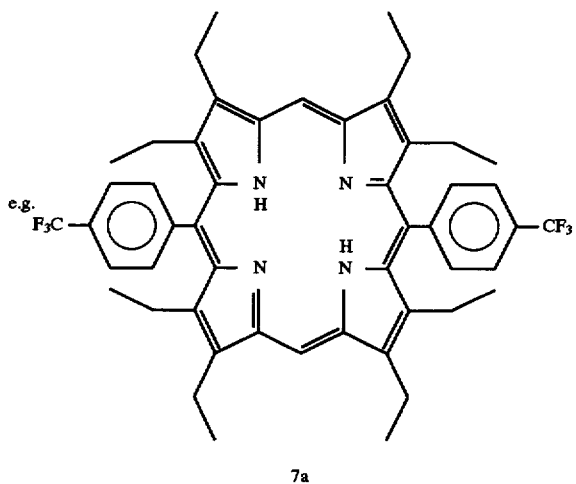

7a

According to this embodiment, a pyrrol compound, 1, produced according to the method of the invention of Section IA, or other source, is combined with an aldehyde or aldehyde precursor in the presence of an acid catalyst as described in Section II. The product di-esterified dipyrromethane may be de-esterified using a lithium halide, as described in Section IB, and further reacted with an aldehyde, a catalytic amount of an organic-solvent-soluble strong acid such as PTSA, HBr, HCl, or $BF_3.OEt_2$ and subsequently oxidized.

As used herein, an aldehyde refers to a compound of general formula $R^{13}CHO$ or $(R^{13}CHO)_n$. $R^{13}$ may be any group which is non-reactive according to the method of the invention. Also $R^{13}$ is preferably selected such that it does not prevent formation of the desired porphyrin under the conditions of the reaction. $R^{13}$ may be selected from the non-exhaustive list, including H, $C_{20}$ alkyl, $C_1$–$C_{20}$ alkenyl, $C_1$–$C_{20}$ cycloalkyl, benzyl, $C_5$–$C_{20}$ aryl; substituted $C_1$–$C_{20}$ alkyl, $C_1$–$C_{20}$ alkenyl, $C_2$–$C_{20}$ cycloalkyl, benzyl, $C_5$–$C_{20}$ aryl, wherein the substitution is one or more $C_1$–$C_{20}$ alkyl, F, Cl, Br, I, OMe, OEt, Me, $CF_3$, $NO_2$ or $NH_2$. In the presence of an acid catalyst as described in Section II.

Therefore, for example, about one equivalent of compound 1, substituted at $R^1$, $R^2$ and $R^3$ as previously described, is added to about 5 equivalents of an aldehyde such as paraformaldehyde or formaldehyde in the presence of an acid catalyst such as HCl, HBr, PTSA, or $BF_3.OEt_2$ to yield the di-esterified dipyrromethane product. After de-esterification by addition of about 5–30 equivalents of LiX in a high boiling polar aprotic solvent such as DMF, 1,3-dimethyl-α-imidazolidine, 2,4,6-collidine, or DMSO, as described in Section I, the product, 5, is mixed with a catalytic mount of PTSA and an aldehyde. The product is subjected to an oxidizing agent, for example, $O_2$, 2,3-dichloro-5,6-dicyanoquinoline, or o-chloranil to yield compound 7. An example of a new asymmetric porphyrin compound synthesized according to the method of the invention is 7a ($R^1=R^2=Et$, $R^{13}=p-C_6H_4CF_3$). Other new porphyrins of general formula 7 which may be produced according to the invention include a compound wherein $R^1$ and $R^2$ are each independently $C_1$–$C_{20}$ alkyl, $C_1$–$C_{20}$ alkenyl, $C_1$–$C_{20}$ cycloalkyl, F, Cl, Br, I, $NO_2$, $NH_2$, OH, OMe, OEt, $SO_3H$; substituted $C_1$–$C_{20}$ alkyl, $C_1$–$C_{20}$ alkenyl, $C_1$–$C_{20}$ cycloalkyl, $C_1$–$C_{10}$ aryl, wherein the substitution includes one or more F, Cl, Br, I, $NO_2$, $NH_2$, OH, OMe, OEt, $SO_3H$ groups; $R^{13}$ is $CF_3$, $CH_2CF_3$, $CF_2CH_3$, $CF_2CF_3$, $CF_3$ substituted phenyl (at the o, m or p position); or a phenyl substituted with one or more F groups.

IV. Preparation of Oxazole Derivatives

Oxazoles are intermediates to pharmaceutically interesting C-acyl-α-amino acids. Another embodiment of the present invention provides for synthesis of oxazoles in high yields through the reaction of isocyanoacetates (compound 21) with acyl chlorides (compound 17) or acid anhydrides (compound 20) in the presence of a strong non-ionic base, for example compound 8, preferably compound 8a. The oxazole product (compound 18) may be further treated, to yield C-acyl-α-amino acids (compound 19) (scheme E). Substitutions on the isocyanoacetate, acyl chloride, and acid anhydrides, ($R^7$, $R^8$, $R^9$, respectively) are selected such that they are non-reactive under the conditions of the reaction. Herein when it is said that a group R (for example ($R^7$, $R^8$ or $R^9$) is non-reactive under the reaction conditions it is meant that the group R is such that it does not participate in the reaction and it does not undergo chemical change or transformation during the reaction. The groups $R^7$, $R^8$ and $R^9$ should also be such that they do not prevent the reaction. Herein when it is said that an R group (for example $R^1$ and $R^2$) should be chosen such that it does not "prevent" reaction, it is meant that the group is selected such that the reactants can react in the manner described; for example, the R groups do not provide sufficient steric hinderance for non-reactivity, nor do they prevent sufficient solubility for reaction.

Herein guidance with respect to "non-reactive" R groups and R groups that do not "prevent" reaction is provided in each instance by representative groups. It is not meant, however, that the lists are exclusive.

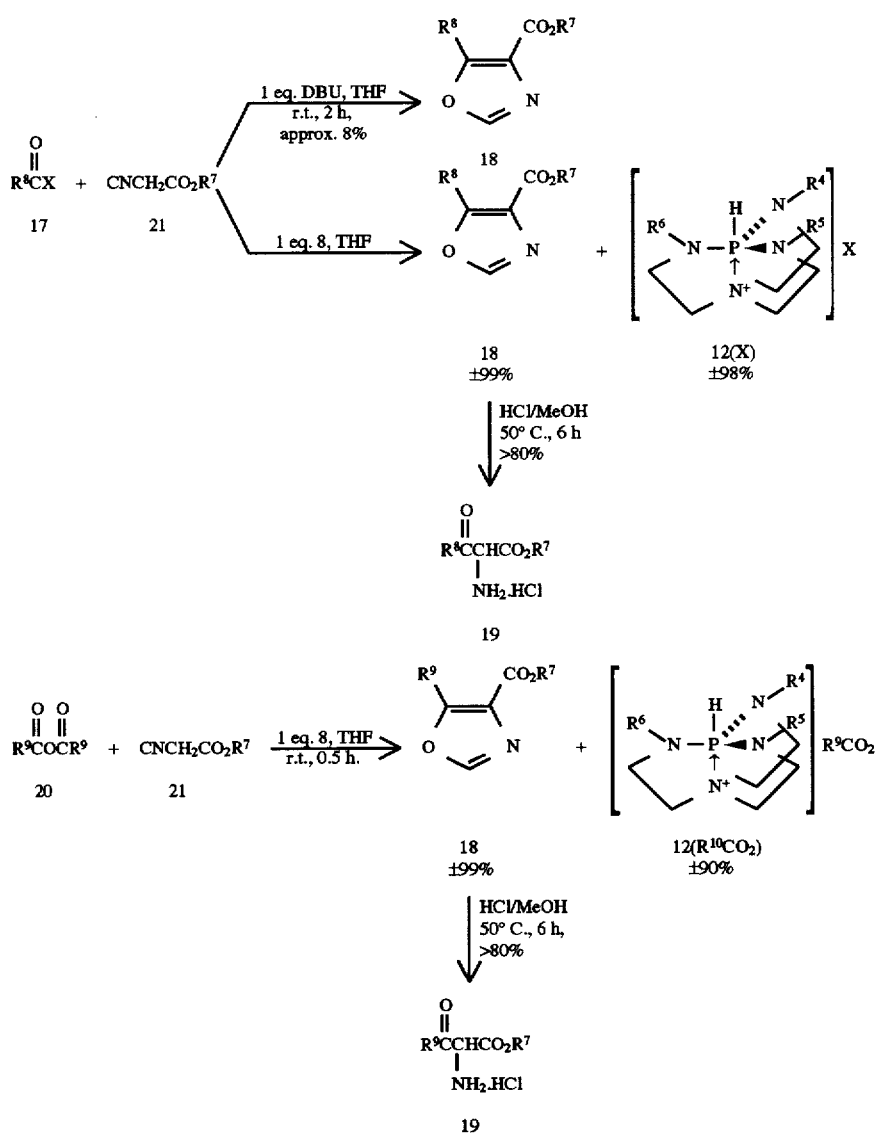

Scheme E

A. Preparation of Oxazoles from Acyl Halides

According to the method of the invention, oxazole compounds of general structure, 18, may be prepared from acyl halides, 17, in greater than 80%, preferably greater than 90%, and typically greater than 98% yield based on the molar equivalent amount of the limiting starting reactant. The method provides for about one molar equivalent of isocyanoacetate and about one equivalent of superbase, 8, preferably 8a, to be mixed with about one equivalent of acyl halide, 17, in a suitable solvent, to yield approximately one molar equivalent of oxazole product 18. It is understood that an excess of base may also be utilized. Superbase parameters are as previously described in Section I.

The reaction is conducted in a suitable organic non-protic solvent. Preferred solvents include THF, DMF, diethylether, or 1,4 dioxane. The R groups ($R^8$ and $R^7$) substituted on the acyl halide and the isocyanoacetate, respectively, may include all R groups that are nonreactive according to the method of the invention and preferably do not prevent formation of the desired oxazole compounds. Preferred substitution of $R^8$ of the acyl halide includes alkyls, alkenyls, aryls and esters. Alkyls and alkenyls may be branched or straight chain. Preferably $R^8=C_1-C_{20}$ alkyl, $C_1-C_{20}$ alkenyl, $C_5-C_{20}$ aryl; $CO_2R$ where $R=H$, $C_1-C_4$ alkyl and unsubstituted benzyl, unsubstituted aryl and $C_1-C_{10}$ substituted benzyl and aryl. X substitution of the acyl halide may be F, Cl, Br, I. Preferred $R^7$ substitutions include alkyls and benzyls, preferably unsubstituted $C_1-C_4$ alkyl and benzyl; $C_1-C_4$ alkyl and benzyl substituted at any carbon with one or more substituents selected from the group consisting essentially of $C_1-C_4$ alkyl F, Cl, Br, I, OMe, OEt, Me, $CF_3$, $NO_2$ or $NH_2$.

Although it is understood that the reactants may be added to the reaction mixture in any order, in a preferred embodiment, the isocyanoacetate, 21, is added to a stirring mixture of solvent and base 8 (preferably 8a) followed by the acyl halide 17. The solvent and one equivalent of superbase is stirred at $-10°$ to $50°$ C., preferably $-5°$ to $10°$ C. Added to the stirring mixture is about one equivalent of isocyanoacetate. The mixture temperature is preferably maintained at about −5° to 10° C. with stirring for about 0–60 minutes. To the stirring mixture of isocyanoacetate and base is then added one equivalent of acyl halide (compound 17). This mixture is stirred at 5°–30° C., preferably about 25° C., for about 30 minutes to 2 hours, until complete formation of oxazole product as indicated by formation of a solid-liquid biphasic system.

As discussed previously, the super base may be recovered upon treatment with t-BuOK. The oxazole product may be isolated by chromatography or recrystallization and stored for future use. Alternatively, the oxazole product may be further reacted, with or without purification, to produce C-acyl-α-amino acid esters.

B. Oxazoles from Acid Anhydrides

According to the present invention, acid anhydrides, 20, in combination with isocyanoacetates, 21, may also be reacted in a suitable solvent to form oxazoles 18. The R groups ($R^7$ and $R^9$) may be any substituent which is non-reactive according to the method of the invention and preferably do not prevent formation of the desired oxazole compounds. $R^7$ may be an alkyl or benzyl, preferably unsubstituted $C_1$–$C_4$ alkyl and benzyl; and $C_1$–$C_4$ alkyl and benzyl substituted at any carbon with one or more substituents selected from the group consisting essentially of $C_1$–$C_4$ alkyl, F, Cl, Br, I, OMe, OEt, Me, $CF_3$, $NO_2$ or $NH_2$. $R^9$ may be an alkyl, alkenyl, aryl, or ester. The alkyls and alkenyls may be branched or straight chain. Preferred $R^9$ substitutions include: $C_1$–$C_{20}$ alkyl, $C_1$–$C_{20}$ alkenyl, $C_5$–$C_{20}$ aryl; $CO_2R$ where R=H, $C_1$–$C_4$ alkyl, unsubstituted benzyl, unsubstituted aryl and $C_1$–$C_{10}$ substituted benzyl or aryl.

The reaction is conducted in a suitable polar or nonpolar solvent such as benzene 1,3-dioxane, diethylether, DMF, or THF. Although the order of addition of reactants may vary, the preferred order follows. To a stirring mixture of solvent and one equivalent of super base compound 8, preferably compound 8a, is added about one equivalent of isocyanoacetate. The mixture is stirred at −10° to 50° C., preferably −5° to 10° C., for about 0–60 minutes. Added to the mixture is about one equivalent of acid anhydride which is stirred at about 0°–50° C., preferably 5°–25° C. for about 30 minutes to 6 hours, typically 1 to 3 hours until complete formation of the oxazole product as indicated by formation of a solid-liquid biphasic system.

The oxazole product, compound 18, may be stored at about 4°–25° C. for future use, or may be further reacted, with or without purification, to form C-acyl-α-amino acid esters.

V. Preparation of C-Acyl-α-Amino Acid Esters

C-acyl-amino acids are useful intermediates in the synthesis of β-hydroxy amino acids, especially β-aryl serines and amino alcohols including sympathomimetic agents such as ephedrine and epineprine. The high-yield efficient method for producing oxazole compounds as described in Section IV may be used to provide the oxazole starting compounds, 18, for the synthesis of C-acyl-α-amino acid esters. (Scheme E.)

Oxazoles produced according to Section IVA and IVB are reacted with an excess of an acid and an alcohol to produce C-acyl-α-amino acid esters. Suitable acids include concentrated HCl, HBr and PTSA. Suitable alcohols include EtOH and MeOH. In a preferred embodiment, oxazole 18, is treated with an excess of HCl-MeOH at about 35°–65° C., preferably about 50° C. The mixture is stirred for about 1 to 12 hours, preferably about 4 to 8 hours until complete as determined by TLC. The product C-acyl-α-amino acid esters (compound 19) are purified by recrystallization or chromatography and stored below 25° C.

EXAMPLES

Example 1

Preparation of 2-ethoxycarbonyl-3,4-diethylpyrrol 1a ($R^1$=$R^2$=$R^3$=Et) by Using the Superbase 8a ($R^1$=$R^2$=$R^3$=$CH_3$)

To a magnetically stirred solution of 4-acetoxy-3-nitrohexane 9a (0.68 g, 3.6 mmol), ethyl isocyanoacetate 10a (0.43 g, 3.6 mmol, 95%) and iso-propanol (0.8 mL) in dry THF (5 mL) at −20° C. was added dropwise a solution of trimethyl proazaphosphatrane 8a (1.6 g, 7.2 mmol) in dry THF (5 mL). The addition funnel was rinsed with 2 mL of dry THF and the rinsing solution was added dropwise to the reaction mixture. The mixture was stirred at −20° C. to −15° C. for 2 h. to form a solid (12(Y))/liquid biphasic system which gave no isocyanoacetate odor when the flask was opened. The solvent was rotary-evaporated in vacuo and the residue was extracted with hexane (20 mL). The precipitate was filtered in vacuo, washed within the filter with diethyl ether (2×10 mL) and dried in vacuo to give $^{31}$P and $^1$H NMR spectroscopically pure solid product 12(Y) (Y=OAc, $NO_2$, mixture, 1.86 g, 96%; M=268). $^{31}$P NMR ($CD_3CN$), 9.2 (Y=$NO_2$) and −9.47 (Y=AcO). $^1$H NMR spectrum ($CDCl_3$) of the mixture of 12($NO_2$) and 12(OAc): 1.98 (s, 3 H, $CH_3CO_2^-$), 2.60 (d, 9 H, $NCH_3$, $^3J_{PH}$=17.4 Hz), 2.98 (dt, 6 H, $N_{eq}CH_2$, $^3J_{PH}$=11.1 Hz, $^3J_{HH}$=6.3 Hz), 3.11 (dt, 6 H, $N_{ax}CH_2$, $^3J_{HH}$=6.0 Hz), 5.27 (d, 1 H, PH, $^1J_{PH}$=494.1 Hz). The combined filtrate and washings were washed with water (15 mL). The organic phase was separated and the aqueous phase was extracted with ethyl acetate (2×25 mL). The combined organic phases were dried with anhydrous $MgSO_4$ and rotary-evaporated in vacuo to give 1a as a $^1$H NMR spectroscopically pure orange oil (0.70 g, 100%). $^1$H NMR ($CDCl_3$): 1.14 (t, 3 H, $CH_3$, $^3J_{HH}$=7.5 Hz), 1.17 (t, partially overlapped with the peak at 1.14, 3 H, $CH_3$, $^3J_{HH}$=7.5 Hz), 1.35 (t, 3 H, $CH_3$, $^3J_{HH}$=7.5 Hz), 2.45 (q, 2 H, $CH_2$, $^3J_{HH}$=7.5 Hz), 2.75 (2 H, $CH_2$, $^3J_{HH}$=7.5 Hz), 4.31 (q, 2 H, $OCH_2$, $^3J_{HH}$=7.5 Hz), 6.67 (d, 1 H, $C_5H$, $^3J_{HH}$=2.7 Hz), 8.76 (br, 1 H, NH). HRMS 195.12593 calcd for $C_{11}H_{17}NO_2$ measured 195.12556.

Example 2

Preparation of 2-ethoxycarbonyl-3,4-diethylpyrrol 1a ($R^1$=$R^3$=Et) Using the Superbase 8a ($R^1$=$R^2$=$R^3$=Me)

Salt 12(Y) can be washed away with water if recovery of 8a is not desired. Thus, the solid-liquid biphasic mixture obtained in the same procedure as in EXAMPLE 1 was rotary-evaporated in vacuo. The residue was mixed with water (15 mL), extracted with ethylacetate (3×25 mL), dried with anhydrous $MgSO_4$, and rotary-evaporated in vacuo to give 1a as a $^1$H NMR spectroscopically pure orange oil (0.70 g, 100%).

Example 3

Recycling Superbase 8a ($R^1$=$R^2$=$R^3$=Me)

To a magnetically stirred suspension of potassium t-butoxide (1.2 g, 0.011 mol) in dry $CH_3CN$ (20 mL) was added dropwise a solution of 12(Y) (Y=$NO_2$, OAc, a mixture, separated in EXAMPLE 1, 1.85 g, 6.9 mmol) in dry $CH_3CN$ (20 mL) by syringe. The mixture was stirred at room temperature for 1 hour and evaporated in vaeuo (oil pump). By cannula, 200 mL of dry pentane was added to the residue which was then stirred overnight. The pentane solution was transferred by cannula to another dry flask (500 mL), from whence it was evaporated in vacuo to give a white solid which was sublimed at 50° C./0.02 torr to give pure 8a (1.22 g, 82%). When this recycled 8a was used for the preparation of 1a, the yield of 1a was the same as that in EXAMPLE 1.

Example 4

Preparation of 2-ethoxycarbonyl-3,4-diethylpyrrol 1a ($R^1=R^2=R^3=Et$) Using the weak base DBU:

(a) To a magnetically stirred solution of 4-acetoxy-3-nitrohexane 9a (0.68 g, 3.6 mmol), ethylisocyanoacetate 10a (0.43 g, 3.6 mmol, 95%) and iso-propanol (0.8 mL) in dry THF (5 mL), was added dropwise a solution of 1,8-diazabicyclo[5.4.0]undec-7-ene (DBU, 1.12 g, 7.37 mmol) in dry THF (5 mL) at 0°–35° C. The addition funnel was rinsed with THF (2 mL) and the rinsing solution was added to the reaction mixture. After stirring at room temperature for 15 h., the mixture was poured into water (15 mL), extracted with ethyl acetate (2×25 mL) and dried with anhydrous $MgSO_4$. The solvent was removed in vacuo to give a mixture of 1a and 16a ($R^1=R^2=R^3=Et$, 0.65 g) in the ratio of 9:1 (as shown by $^1H$ NMR integration for the $C_5$—H). $^1H$ NMR ($CDCl_3$) of 16a: 7.43 (d, $^2J_{HH}$=2.6 Hz), other peaks were overlapped with the peaks of 1a. HRMS of the mixture of 1a and 16a: 1a calcd 195.12593 for $C_{11}H_{17}NO_2$, measured 195.12546; 16a, calcd 239.13270 for $C_{12}H_{17}NO_4$, measured 239.13213. (b) The same reaction was conducted at −20° to −15° C. for 2 h. The reaction mixture was then poured into water (15 mL) and rotary evaporated in vacuo to remove THF. The residue was then diluted with water (5 mL) and extracted with ethyl acetate (2×25 mL). The extracts were dried with anhydrous $MgSO_4$ overnight, and rotary evaporated in vacuo to give 0.68 g of a brown liquid with a heavy isocyanoaeetate odor. The brown oil displayed a complicated $^1H$ NMR spectrum consistent with mainly starting material 9a and 10a with nearly no detectable 1a.

Example 5

Preparation of 2-methoxycarbonyl-3,4-diethylpyrrol 1b ($R^1=R^2=Et$, $R^3=Me$) Using the Superbase 8a ($R^1=R^2=R^3=Me$)

To a magnetically stirred solution of 4-acetoxy-3-nitrohexane (4.80 g, 25.0 mmol), methyl isocyanoacetate 10b (2.64 g, 25.0 mmol, 95%) and iso-propanol (6.5 mL) in dry THF (15 mL) at −20° C. was added dropwise a solution of trimethyl proazaphosphatrane 8a (10.95 g, 50.69 mmol) in dry THF (15 mL). The mixture was stirred at −20° to −15° C. for 2 h. to form a solid-liquid biphasic system which was rotary evaporated to dryness. The residue was stirred with hexane (80 mL) for 30 min. The precipitate was filtered in vacuo, washed with ether (2×30 mL) and dried in vacuo to give $^{31}P$ and $^1H$ NMR spectroscopically pure 12(Y) (Y=$NO_2$, OAc mixture, 12.8 g, 95%). The combined filtrate and washings were washed with water (20 mL) and the organic layer was separated. The aqueous layer was extracted with ethyl acetate (2×50 mL), the combined organic phases were dried with anhydrous $MgSO_4$ and rotary evaporated in vacuo to give 1b as a $^1H$ NMR spectroscopically pure orange oil (4.57 g, 100%). $^1H$ NMR ($CDCl_3$): 1.13 (t, 3 H, $CH_3$,$^3J_{HH}$=7.5 Hz), 1.89 (t, 3 H, $CH_3$,$^3J_{HH}$=7.5 Hz), 2.46 (q, 2 H, $CH_2$,$^3J_{HH}$=7.4 Hz), 2.75 (q, 2 H, $CH_2$,$^3J_{HH}$=7.5 Hz), 3.84 (s, 3 H, $OCH_3$), 6.67 (d, 1 H, $C_5H$, $^2J_{HH}$=2.7 Hz), 8.77 (br, 1 H, NH). For elemental analysis, a small mount of sample was recrystallized from hexane in a freezer. The supernatant was removed by syringe to give light yellowish crystals which were dried in vacuo. HRMS: calcd 181.11028 for $C_{10}H_{15}NO_2$, measured 181.11008. Elemental analysis: calcd C, 66.26; H, 8.35; N, 7.33. Found C, 66.03; H, 8.25; N, 7.98.

Example 6

Preparation of 2-ethoxycarbonyl-3,4-butylenepyrrol 1c ($R^1=R^2=CH_2CH_2CH_2CH_2$, $R^3=Et$) Using the Superbase 8a ($R^1=R^2=R^3=Me$)

To a solution of 1-nitrocyclohexene 11c (0.66 g, 5.2 mmol) and ethyl isoeyanoacetate 10a (0.62 g, 5.2 mmol, 95%) in dry THF (5 mL) at −20° C. was added dropwise a solution of trimethyl proazaphosphatrane 8a (1.12 g, 5.23 mmol) in THF (5 mL). The addition funnel was rinsed with 2 mL of dry THF which was then added dropwise to the reaction mixture. The mixture was stirred at −20° to −15° C. for 2 h. and evaporated in vacuo to dryness. The residue was stirred with hexane (25 mL) for 30 min and filtered in vacuo. The solid was washed with ether (2×10 mL) and dried in vacuo to give 12($NO_2$) (1.28 g, 94%). $^{31}P$ NMR ($CD_3CN$) of 12($NO_2$): −9.27. The combined filtrate and washings were washed with water (10 mL) and then the organic layer was separated. The aqueous layer was extracted with ethyl acetate (2×30 mL) and the combined organic layers were then dried with anhydrous $MgSO_4$ overnight, evaporated in vacuo to give 1c (1.0 g, 100%) as a $^1H$ NMR spectroscopically pure solid. $^1H$ NMR ($CDCl_3$): 1.32 (t, 3 H, $CH_3$, $^3J_{HH}$=6.9 Hz), 1.72 (m, 4 H, $CH_2$), 2.52 (t, 2 H, $CH_2$, $^3J_{HH}$=5.7 Hz), 2.79 (t, 2 H, $CH_2$, $^3J_{HH}$=4.2 Hz), 4.27 (q, 2 H, $OCH_2$, $^3J_{HH}$=6.9 Hz), 6.62 (d, 1 H, $C_5H$, $^3J_{HH}$=2.4 Hz), 8.87 (br, 1 H, NH). HRMS: calcd 193.11028 for $C_{11}H_{15}NO_2$, measured 193.11045.

Example 7

Preparation of 2-ethoxycarbonyl-3-trifluoromethyl-4-ethylpyrrol 1d ($R^1=Et$, $R^2=CF_3$, $R^3=Et$) Using the Superbase 8a ($R^1=R^2=R^3=Me$)

To a magnetically stirred solution of 2-acetoxy-3-nitro-1,1,1-trifluorobutane (1.99 g, 9.25 mmol), 9b prepared by using the method of OhO, N. et. al., *Bull. Chem. Soc. Jap.*, 62:3386 (1989), ethyl isocyanoaeetate (1.10 g, 9.25 mmol, 95%) and iso-propanol (2.5 mL) in dry THF (5 mL) at −20° C. to −15° C. was added dropwise to a solution of trimethyl proazaphosphatrane, 8a (4.0 g, 18.5 mmol) in THF (5 mL). The addition funnel was rinsed with 2 mL of dry THF and the rinsing solution was added to the reaction mixture. The mixture was stirred at −20° C. to −15° C. for 2 h. to form a solid (12(Y))/liquid biphasic system which gave an isocyanoacetate odor when the flask was opened. The solvent was removed and the residue was mixed with water (20 mL) and extracted with hexane (3×50 mL). The combined extracts were dried with $MgSO_4$ and rotary evaporated to give 1d as a $^1H$ NMR spectroscopically pure oil (2.16 g, 100%) $^1H$ NMR ($CDCl_3$): 1.20 (t, 3H, $CH_3$, $^3J_{HH}$=7.5 Hz), 1.36 (t, 3H, $CH_3$, $^3J_{HH}$=7.5 Hz), 2.62 (q, 2H, $CH_2$, $^3J_{HH}$=7.5 Hz), 4.38 (q, 2H, $CH_2$, $^3J_{HH}$=7.5 Hz), 6.73 (d, 1H, $C_5H$, $^3J_{HH}$=1.8 Hz), 9.51 (br, 1H, NH); HRMS 235.08201 calcd from $C_{10}H_{12}F_3NO_2$, measured 235.08222.

Example 8

Preparation of 2-t-butoxycarbonyl-3-methoxycarbonylethyl-4-Methyl pyrrol 1e ($R^1=Me$, $R^2=CH_2CH_2CO_2Me$, $R^3=t$-Bu) Using the Superbase 8a ($R^1=R^2=R^3=Me$)

To a magnetically stirred solution of 5-acetoxy-4-nitrohexane 9c (0.83 g, 3.5 mmol), t-butyl isocyanoacetate (0.53 g, 3.5 mmol, 95%) and iso-propanol (0.5 mL) in dry THF (5 mL) at −20° C. to −15° C. was added dropwise a solution of 8a (1.548 g, 9.7 mmol) in THF (5 mL). The addition funnel was rinsed and the rinsing solution was added to the reaction mixture. The mixture was stirred at −20° to −15° C. for 2.0 hours to form a solid (12(Y))/liquid biphasic system which gave no isocyanoacetate odor when the flask was opened. The solvent was rotary evaporated in vacuo. The residue was mixed with water (20 mL) and extracted with hexane (3×50 mL). The extracts were dried with $MgSO_4$ and then rotary evaporated to give a $^1H$ NMR spectroscopically pure oil 9e (0.94 g, 100%). $^1H$ NMR ($CDCl_3$): 1.56 (s, 94, $CCCH_3)_3$), 2.26 (s, 3 H, $C_4$—CH), 2.53 (t, 2 H, $CH_2$, $^3J_{HH}$=7.5 Hz), 2.75 (t, 2 H, $CH_2$, $^3J_{HH}$=7.5 Hz), 3.67 (s, 3 H, $OCH_3$), 6.65 (d, $^1H$, $C_5H$, $^3J_{HH}$=3. Hz), 8.86 (br, $^1H$, NH); HRMS 267.16706 for $C_{14}H_{21}NO_4$, measured 267.16735.

Example 9

Preparation of 3,4-diethylpyrrol 3a ($R^1$=$R^2$=Et) Using LiX

A mixture of 2-methoxycarbonyl-3,4-diethylpyrrol 1b (1.0 g, 55 mmol) which was prepared in EXAMPLE 5, lithium chloride (2.4 g, 0.055 mol) and water (0.1 g, 6 mmol) in DMSO (25 mL) was de-aerated with argon for 10 min. and then refluxed for 1.5 h. TLC (silica gel plate hexane:diethylether=5:1) showed that all of the starting material 1b had disappeared and that a new composition (3a) was formed. The mixture was poured into 100 g of ice-$H_2O$ and extracted with diethyl ether (3×50 mL). The combined organic layers were washed with saturated sodium chloride (15 mL) and rotary evaporated in vacuo to give 3a (0.68 g, 100%) as a $^1H$ NMR spectroscopically pure oil. $^1H$ NMR ($CDCl_3$): 1.20 (t, 6 H, $CH_3$, $^3J_{HH}$=7.5 Hz), 2.46 (q, 4 H, $CH_2$, $^3J_{HH}$=7.5 Hz), 6.52 (d, 2 H, $C_2H$ and $C_5H$; $^3J_{HH}$=2.4 Hz), 7.81 (br, 1 H, NH). HRMS: calcd 122.10480 for $C_8H_{13}N$, measured 123.10483.

The same reaction was conducted with LiBr (10 equivalents) and LiI (10 equivalents). The time needed for complete conversion of 1b into 3a was 2.0 h. for LiBr and 3.0 h. for LiI. The yield of 3a in both cases was 100%. When the reaction was conducted with NaCl, however, no product 3a was formed upon 3 h. refluxing as shown by TLC.

2-Ethoxycarbonyl-3,4-diethylpyrrol was also de-ethylated and subsequently decarboxylated by LiCl, but the reaction was slower.

Example 10

Preparation of 3,4-diethylpyrrol 3a ($R^1$=$R^2$=Et) Using NaOH

To a solution of 1a (1.0 g, 5.1 mmol, prepared in EXAMPLE 4) in 95% ethanol (5 mL) was added in one portion a sodium hydroxide (0.32 g, 8.2 mmol) solution in water (0.7 mL). The solution was de-aerated with argon for 10 min. and then refluxed for 2 h. Following this, 5 mL of ethanol was distilled out at an oil bath temperature of 110° C. The residue was mixed with water (3.5 mL) and refluxed under argon for 6.5 h., cooled to r.t. and extracted with diethylether (3×20 mL). The solvent was removed in vacuo to give a red-brown liquid 3a (0.31 g, 49%) which was contaminated with unreacted 1a as shown by $^1H$ NMR spectroscopy. The aqueous layer was diluted with water (10 mL), neutralized with dilute hydrochloric acid and extracted with ether (2×20 mL). The aqueous layer was washed with 10% $NaHCO_3$ solution (10 mL) and extracted again with diethyl ether (2×20 mL). The combined ether phases were washed with 10% $NaHCO_3$ (5 mL) and evaporated in vacuo to give the sodium salt of 3,4-diethylpyrrolcarboxylate as a grey solid (0.48 g, 50%). $^1H$ NMR ($CDCl_3$): 1.16 (t,3 H, $CH$, $^3J_{HH}$=7.5 Hz), 1.20 (t, 3 H, $CH_3$, $^3J_{HH}$=7.5 Hz), 2.46 (t, 2 H, $CH_2$, $^3J_{HH}$=7.5 Hz), 2.78 (t, 2 H, $CH_2$, $^3J_{HH}$=7.5 Hz), 6.74 (d, 1 H, $C_5H$, $^3J_{HH}$=2.7 Hz), 8.92 (br, 1 H, NH). (b) To a solution of 1a (1.0 g, 5.1 mmol) in 95% ethanol (5 mL) was added in one portion a sodium hydroxide (0.32 g, 8.2 mmol) solution in water (0.7 mL). The solution was de-aerated and then refluxed for 6.5 h. Ethanol was then distilled out at an oil bath temperature of 110° C. After cooling to r.t., the residue was dissolved in a mixture of ethanol (1 mL) and water (3.5 mL), the resulting solution refluxed for 19 h. under argon and extracted with diethyl ether (3×40 mL) to give 0.17 g of an unidentified solid.

Example 11

Preparation of bis-2-(5-methoxycarbonyl-3,4-diethylpyrro)methane 4a ($R^1$=$R^2$=Et, $R^3$=Me)

A mixture of 2-methoxycarbonyl-3,4-diethylpyrrol 1a (0.40 g, 2.2 mmol, prepared in EXAMPLE 1), paraformaldehyde (0.26 g, 8.6 mmol), ethanol (2.5 mL) and concentrated hydrochloric acid (0.05 mL) was refluxed for 30 min under argon, cooled to room temperature and then kept in a freezer overnight at about −20° C. The resulting crystals were filtered in vacuo to give a white solid (0.36 g, 87.5%), m.p. 130°–131° C. $^1H$ NMR ($CDCl_3$): 1.06 (t, 6 H $CH_3$, $^3J_{HH}$=7.5 Hz), 1.15 (t, 6 H, $CH_3$, $^3J_{HH}$=7.5 Hz), 2.42 (q, 4 H, $CH_2$, $^J_{HH}$=7.5 Hz), 2.72 (q, 4 H, $CH_2$, $^3J_{HH}$=7.5 Hz), 3.80 (s, 6 H, $OCH_3$), 3.87 (s, 2 H, $CH_2$), 8.63 (br, 2 H, NH). HRMS: calcd 374.22056 for $C_{21}H_{30}N_2O_4$, measured 374.22025. Elemental analysis: calcd C, 67.34, H, 8.08; N, 7.48. Found C, 67.37, H, 8.00, N, 6.87.

Example 12

Preparation of bis-2-(5-ethoxycarbonyl-3-trifluoromethyl-4-ethyl pyrro)methane 4b ($R^1$=Et, $R^2$=$CF_3$, $R^3$=Et)

A solution of 2-ethoxy carbonyl-3-trifluoromethyl-4-ethyl pyrrol 1d (0.25 g, 1.1 mmol), $CH_2(OMe)_2$ (0.41 g, 5.4 mmol) and $BF_3.OEt_2$ (0.1 g, 0.7 mmol) in dry $CH_2Cl_2$ (10 mL) under argon was stirred at room temperature for 35 h. TLC showed complete conversion of 1d to 4b. The solvent was removed under vacuum and the residue was washed with 10% sodium bicarbonate (40 mL) and extracted with ethyl acetate (3×50 mL). The extracts were dried with sodium sulfate and rotary evaporated to give a white solid which was purified by flash chromatography using $CH_2Cl_2$ as eluting solvent to give pure 4b (0.23 g, 88.5%). $^1H$ ($CDCl_3$): 0.89 (t, 6 H, $CH_3$, $^3J_{HH}$=7.5 Hz), 1.29 (t, 3 H, $CH_3$, $^3J_{HH}$=7.5 Hz), 2.48 (q, 4 H, $CH_2$, $^3J_{HH}$=7.5 Hz), 4.25 (q, 4 H, $CH_2$, $^3J_{HH}$=7.5 Hz), 3.97 (s, 2 H, $CH_2$), 10.23 (br, 2 H, NH); $^{13}C$ NMR ($CD_2Cl_2$): 14.00 (s, $CH_3$), 16.03 (s, $CH_3$), 18.48 (g, $CH_2$, $^4J_{FC}$=2.1 Hz), 22.26 (s, $C_5CH_2$), 61.9 (s, $OCH_2$), 116.86 (q, $C_3$, $^2J_{CF}$=38.1 Hz), 120.26 (q, $C_4$, $^3J_{FC}$=3.8 Hz), 123.94 (q, $CF_3$, $^1J_{FC}$=268.9 Hz), 125.15 (q, cd, $J_{FC}$=1.6 Hz), 129.05 (s, $C_5$), 160.44 (s, C=O); HRMS 482.16403 calcd for $C_{21}H_{24}F_6N_2O_4$, measured 482.16389. Elementary analysis: calcd C, 52.26, H, 5.02, N, 5.81, found C, 52.22, H, 4.84, N, 5.82.

PTSA was also used as an acid catalyst but the reaction was much slower and needed more than 10 days to complete.

Preparation of bis-2-(3-trifluoromethyl-4-ethyl pyrro) methane 5b is accomplished by further reacting 4b with lithium chloride and DMSO as described in Example 13.

Example 13

Preparation of bis-2-(3,4-diethylpyrro)methane 5d
($R^1=R^2=Et$)

A mixture of bis-2-(5-methoxycarbonyl-3,4-diethylpyrro) methane 4a (0.26 g, 0.69 mmol), lithium chloride (0.60 g, 0.014 mol), water (26 mg, 1.4 mmol) and DMSO (10 mL) was de-aerated with argon for 10 min. and refluxed under argon for 2 h. The mixture was poured into ice-$H_2O$ (50 g), and extracted with diethylether (2×50 mL). The organic phase was washed with saturated sodium chloride (10 mL) and rotary evaporated in vacuo to give 5d (0.18 g, 100%) as a $^1$H NMR spectroscopically pure oil. $^1$H NMR (CDCl$_3$): 1.12 (t, 6 H, CH$_3$, $^3J_{HH}$=7.5 Hz), 1.22 (t, 6 H, CH$_3$, $^3J_{HH}$=7.5 Hz), 2.38 to 2.51 (m, 8 H, CH$_2$), 3.84 (s, 2 H, CH$_2$), 6.39 (d, 2 H, C$_5$H, $^3J_{HH}$=2.3 Hz), 7.48 (br, 2 H, NH). HRMS: calcd 258.20960 for C$_{17}$H$_{26}$N$_2$, measured 258.20916.

Example 14

Preparation of 1,2,3,4,5,6,7,8-octaethylporphyrin 6a
($R^1=R^2=Et$)

To a stirred suspension of LiAlH$_4$ (0.41 g, 0.011 mol) in dry THF (15 mL) at 0° C. to 3° C. was added dropwise a solution of 2-ethoxycarbonyl-3,4-diethylpyrrol 1a (0.70 g, 3.6 mmol, prepared in EXAMPLE 1) in THF (15 mL). The addition funnel was rinsed with THf (2 mL) and the rinsing solution was added dropwise to the reaction mixture. The mixture was stirred at 0°-3° C. for 2 h. and then 5 mL of ethyl acetate was added followed by 30 mL of saturated ammonium chloride to destroy excess LiAlH$_4$. The solid was filtered off and washed with ethyl acetate (40 mL). The organic phase was separated and the aqueous phase was extracted with ethyl acetate (2×30 mL). The combined organic phases were rotary-evaporated in vacuo at room temperature (using ice-$H_2O$ as a recycling coolant to accelerate evaporation of solvent) to give a light-yellowish oil 2a ($R^1=R^2=Et$). To a solution of the crude, undried 2a and dimethoxymethane (2.7 g, 0.036 mol) in CH$_2$Cl$_2$ (15 mL, dried with P$_4$O$_{10}$) was added PTSA.H$_2$O (0.11 g, 0.59 mmol). The mixture, which was contained in an aluminum-foil-wrapped flask, was stirred at room temperature for 24 h. o-Chloranil (1.0 g, 4.1 mmol) in CH$_2$Cl$_2$ (10 mL) was added in one portion to the red reaction mixture, which was then stirred at room temperature for another 24 h. Finally, the mixture was washed with 1N NaOH (50 mL) and extracted with CHCl$_3$ (3×100 mL). The combined organic phases were rotary-evaporated and chromatographed on aluminum oxide (basic, activated, Brochman I, 2.5×17 cm) using CHCl$_2$ as eluent. After evaporation of the eluent, the product was recrystallized from CHCl$_3$—MeOH to give pure OEP 6a (0.33 g, 69%). $^1$H NMR. (CDCl$_3$): -3.75 (br, 2 H, NH), 1.92 (t, 24 H, CH$_3$, $^3J_{HH}$=7.5 Hz), 4.10 (q, 16 H, CH$_2$, $^3J_{HH}$=7.5 Hz), 10.10 (s, 4 H, meso-H). UV-vis (CHCl$_3$): λmax 398, 498, 534, 566, 620. HRMS: calcd 534.37225 for C$_{36}$H$_{46}$N$_4$, measured 534.37072. Compound 6a is an example of a porphyrin wherein $R^1$ and $R^2$ are all ethyl groups. Alternatively, in another example of a porphyrin molecule, all $R^1$ could be the same and all $R^2$ could be the same with $R^1$ being different from $R^2$.

It was found that (1) The combined organic phases containing crude 2-hydroxymethyl-3,4-diethylpyrrol 2a obtained from the LiAlH$_4$ reduction reaction should not be stored or dried if a high yield of OEP 6a was desired, because 2a is not stable. (2) Dimethoxymethane was used as a dehydration agent to remove water formed from the acid-catalyzed condensation reaction of 2a. Basic or neutral aluminum oxide was preferred for fast separation with a smaller amount of eluting solvent. Methylene chloride was preferred as the eluting solvent.

TABLE L

Preparation of OEP (6a) from 1a*.

| Expt. | Treatment of crude 2a | Condensation Reaction Conditions | Yield of OEP % |
|---|---|---|---|
| 1 | not dried but immediately used | CH$_2$Cl$_2$, PTSA-H$_2$O CH$_2$(OMe)$_2$ (10 eq) | 69 |
| 2 | dried with MgSO$_4$ for 12 h | CH$_2$Cl$_2$, PTSA-H$_2$O CH$_2$(OMe)$_2$ (10 eq) | 21 |
| 3 | not dried but immediately used | CH$_2$Cl$_2$, PTSA-H$_2$O | 53 |
| 4 | not dried but immediately used | CH$_2$Cl$_2$, PTSA-H$_2$O (CH$_2$O)$_n$ (10 eq) | 23 |

*In all four experiments, o-chloranil was used as the oxidant, basic aluminum oxide was used as the chromatography packing material and CH$_2$Cl$_2$ was employed as the eluting solvent.

Example 15

Preparation of 1,2,-3,4-5,6-7,8-tetrabutylenylporphyrin 6b
($R^1R^2=R^1R^{2'}=R^{1''}R^{2''}=R^{1'''}R^{2'''}=CH_2CH_2CH_2$)

To a suspension of LiAlH$_4$ (0.65 g, 0.016 mmol) in dry THF (20 mL) was added dropwise at 0°-3° C. a solution of 2-ethoxycarbonyl-3,4- butylenylpyrrol 1c (1.0 g, 5.2 mmol, prepared in EXAMPLE 6) in dry THF (15 mL). The addition funnel was rinsed with dry THF (2 mL) and the rinsing solution was added dropwise to the reaction mixture. After the reaction mixture was stirred at 0°-3° C. for 2 h., 5 mL of ethyl acetate and 40 mL of saturated ammonium chloride were added to destroy excess LiAlH4. The solid was filtered off in vacuo and washed with ethyl acetate (50 mL). The organic phase was separated and the aqueous phase was extracted with ethyl acetate (2×40 mL), washed with saturated sodium chloride and rotary-evaporated in vacuo at room temperature (using ice-H$_2$O as a recycling coolant). To the residue was added dry CH$_2$Cl$_2$ (20 mL), dimethoxymethane (3.4 g, 0.052 mol) and PTSA.H$_2$O (0.21 g, 1.1 mmol). The mixture, which was contained in an aluminum-foil-wrapped flask, was stirred at room temperature for 24 h. o-Choranil (1.53 g, 6.22 mmol) in CH$_2$Cl$_2$ (10 mL) was added to the reaction mixture, which was then stirred for another 24 h. Finally, the reaction mixture was washed with 1N NaOH solution, extracted with CHCl$_3$ (3×100 mL) and chromatographed on aluminum oxide (basic, activated, Brochman I, 2.5×15 cm). The product obtained upon evaporation was recrystallized from CHCl$_3$—MeOH to give pure 6b (0.44 g, 65%). $^1$HNMR (CDCl$_3$): -3.84 (br, 2 H, NH), 2.49 (br, 16 H), 4. 11 (br, 16 H), 9.88 (5, 4 H). UV-vis(CHCl$_3$): λmax 398, 498, 534, 566, 618. HRMS: calcd 526.30966 for C$_{36}$H$_{38}$N$_4$, measured 526.30885.

Example 16

Preparation of 1,2,3,4,5,6,7,8-octaethyl-9,11-bis[p-trifluoromethyl-phenyl]porphyrin 7a ($R^1=R^2=Et$, $R^{13}=C_6H_4$-p-CF$_3$)

A solution of 5d (0.18 g, 0.69 mmol, prepared in EXAMPLE 13, and p-CF$_3$ benzaldehyde (0.12 g, 0.69 mmol) in methanol (15 mL) was deaerated with argon for 10 min. and PTSA.H$_2$O (0.035 g, 0.18 mmol) was added to the aluminum-foil-wrapped flask. The mixture was stirred at room temperature for 30 min. under argon and allowed to stand in the dark for 17.5 h at about 5° C. for 20 h. The methanol was removed in vacuo and the residue was dissolved in THF (40 mL). A solution of 2,3-dichloro-5,6-dicyclobenzoquinone (0.53 g, 0.0023 mol) in THF (10 mL) was added over 5 min. The flask was then stirred for 7.0 h and the solvent removed in vacuo. The residue was dissolved in CHCl$_3$ (5 mL), layered with a mixture of methanol (25 mL) and triethylamine (7 mL) and allowed to stand for 24 h. The solid was filtered and dried in vacuo to give 0.105 g of fine purple crystals (41.3%). $^1$H NMR (CDCl$_3$): −2.10 (br, 2 H), 1.16 (t, 12 H, CH$_3$, $^3J_{HH}$=7.4 Hz), 1.85 (t, 12 H, CH$_3$, $^3J_{HH}$=7.5 Hz), 2.75 (q, 8 H, CH$_2$, $^3J_{HH}$=7.5 Hz), 4.00 (q, 8 H, CH$_2$, $^3J_{HH}$=7.5 Hz), 7.96 (d, 4 H, Ar—H, $^3J_{HH}$=7.8 Hz), 8.36 (d, 4 H, Ar—H, $^3J_{HH}$=7.8 Hz), 10.26 (s, 2 H). UV-vis (CHCl$_3$): λmax 410, 510, 544, 578, 628. HRMS: calcd 822.40962 for C$_{50}$H$_{52}$F$_6$N$_4$, measured 822.40904.

Example 17

Preparation of 4-methoxycarbonyl-5-(3,4,5-trimethoxyphenyl)oxazole 19a (R$^8$=3,4,5-trimethoxyphenyl, R$^7$=Me) Using the Superbase 8a (R$^4$=R$^5$=R$^6$=Me)

To a magnetically stirred solution of the Superbase 8a (0.47 g, 2.1 mmol) in dry THF (5 mL) at 5° C. was added in one portion methyl isocyanoacetate 21b (0.23 g, 2.1 mmol, 95%). The solution was stirred for 15 min. To this stirred solution was added dropwise a solution of 3,4,5-trimethoxybenzoylchloride 17a (0.50 g, 2.1 mmol, 98%) at 5° C. The reaction mixture was then stirred at room temperature for 30 min. to form a solid-liquid biphasic system lacking an isocyanoacetate odor when the flask was opened. The biphasic mixture was diluted with ethylacetate (40 mL) and filtered in vacuo. The solid was washed with ethylacetate (2×10 mL) within the filter and dried in vacuo to give $^{31}$P NMR and $^1$H NMR. spectroscopically pure 12(Cl) (0.52 g, 98%). $^{31}$P NMR (CD$_3$CN): −9.40. $^1$H NMR (CD$_3$CN): 2.60 (d, 9 H, NCH$_3$ $^3J_{PH}$=17.4), 2.98 (dt, 6 H, N$_{eq}$CH$_2$, $^3J_{PH}$=11.1 Hz), $^3J_{HH}$=6.0 Hz), 3.12 (dt, 6 H, N$_{ax}$CH$_2$, $^3J_{PH}$=5.7 Hz, $^3J_{HH}$=6.0 Hz), 5.28 (d, 1 H, PH, $^1J_{PH}$=493.8 Hz). The combined flitrate and washings were washed with water (5 mL). The organic phase was separated and the aqueous phase was extracted with ethyl acetate (15 mL). The combined organic phases were dried over anhydrous MgSO$_4$ and rotary-evaporated to give $^1$H NMR spectroscopically pure 18a (0.61 g, 99%). $^1$H NMR (CD$_3$CH): 3.78 (s, 3H, OCH$_3$), 3.84 (s, 3H, OCH$_3$), 3.85 (s, 6 H, OCH$_3$), 7.37 (s, 2 H, NH—H), 8.06 (s, 1 H, C$_2$H,). HRMS: calcd 293.08994 for C$_{14}$H$_{15}$NO$_6$, measured 293.08940.

Example 18

Preparation of 4-methoxycarbonyl-5-(3,4,5-trimethoxyphenyl)oxazole 18a (R$^8$=3,4,5-trimethoxyphenyl, R$^7$=Me) Using the Weak Base DBU To a stirred solution of methyl isocyanoacetate 21b (0.44 g, 4.2 mmol, 95%) in dry THF (5 mL) at 5° C. was added DBU (0.63 g, 4.2 mmol). After the solution was stirred for 45 min, a solution of 3,4,5,-trimethyoxybenzoylchloride (0.99 g, 4.2 mmol) in THF (10 mL) was added dropwise at 5° C. The mixture was then further stirred at room temperature for 2 h. to give a brown solution with a heavy isocyanoacetate odor when the flask was opened. The solution was rotary evaporated, washed with water (10 mL) and extracted with ethyl acetate (2×35 mL). The combined organic extracts were rotary evaporated in vacuo to give a brown oil (0.68 g). The $^1$H NMR spectrum showed that this brown oil contained mainly unreacted methylisocyanoacetate and the hydrolyzed form of trimethoxybenzoylchloride, with a small amount of the desired 4-methoxycarbonyl-5-(3,4,5-trimethoxyphenyl) oxazole 18a. Gas chromatography of this mixture showed that only ~8% of 18a had formed.

Example 19

Preparation of 4-methoxycarbonyl-5-phenyloxazole 18b (R$^9$=Ph, R$^7$=Me) Using the Strong Base 8a (R$^4$=R$^5$=R$^7$=Me)

To a solution of the base 8a (0.91 g, 4.2 mmol) in dry THF (5 mL) at 5° C. was added by syringe methyl isocyanoacetate (0.44 g, 4.2 mmol, 95%). After the solution was stirred at 5° C. for 15 min., a solution of benzoylanhydride 20a (R$^9$=Ph, 0.97 g, 4.2 mmol) in dry THF (5 mL) was added at 5° C. The mixture was then stirred at room temperature for 30 min. to form a solid-liquid hipbasic system without the odor of the isocyanoacetate when the flask was opened. The biphasic mixture was rotary-evaporated in vaeuo and the residue was treated with diethylether (30 mL) followed by filtration in vacuo. The solid was washed within the filter with ether (3×10 mL) and dried in vacuo to give 12(PhCO$_2$) (1.30 g., 91%). $^{31}$P NMR (CD$_3$CN): −9.52. $^1$H NMR (CD$_3$CN): 2.58 (d, 9 H, NCH$_3$, $^3J_{PH}$=17.4 Hz), 2.96 (dt, 6 H, N$_{eq}$CH$_2$, $^3J_{PH}$=11.4 Hz, $^3J_{HH}$=6.0 Hz), 3.10 (dt, 6 H, N$_{ax}$CH$_2$, $^3J_{PH}$=7.2 Hz, $^3J_{HH}$=6.0 Hz), 5.28 (d, 1 H, PH, $^1J_{PH}$=493.8 Hz), 7.23 and 7.89 (two m, 5 H, C$_6$H$_5$). The flitrate and the washings were combined and washed with water (10 mL). The organic phase was separated and the aqueous phase was extracted with ethyl acetate (20 mL). The combined organic phases were rotary evaporated in vacuo to give $^1$H NMR spectroscopically pure 18b (0.85 g, 100%). $^1$H NMR (CD$_3$CN): 3.83 (s, 3 H, OCH$_3$), 7.49 and 7.96 (two m, 5 H, C$_6$H$_5$), 8.03 (s, 1 H, C$_2$H). HRMS: calcd 203.05824 for C$_{11}$H$_{19}$NO$_3$, measured 203.05833.

Example 20

Preparation of α-(3,4,5-trimethoxyphenyl) acylaminoacid methyl ester 19a (R$^8$=3,4,5-trimethoxyphenyl, R$^7$=Me)

The oxazole 18a prepared in EXAMPLE 18 (0.61 g, 2.1 mmol) was dissolved in a mixture of methanol (15 mL) and concentrated hydrochloric acid (5 mL). The solution was stirred at 50° C. for 6 h. and then rotary-evaporated to remove methanol. To the residue was added water (20 mL) and the acidic solution was then washed with diethylether (10 mL). The separated aqueous layer was rotary evaporated in vacuo below 30° C. The residue was dissolved in methanol and the resultant solution was then evaporated in vacuo to dryness. This treatment was repeated four times to remove excess hydrochloric acid. The resulting precipitate was recrystallized from ethyl acetate-methanol to give pure 19a (0.55 g, 82%), m.p. 175°–176° C. $^1$H NMR (DMSO-d$_6$): 3.71 (s, 3 H, OCH$_3$), 3.79 (s, 3 H, OCH$_3$), 3.79 (s, 3 H, OCH$_3$), 3.87.(s, 6 H, OCH$_3$), 6.34 (s, 1 H, CH), 7.47 (s, 2 H, C$_6$H$_2$), 9.11 (br, 3 H, NH$_3^+$). Mass (FAB): 284 (M—Cl)$^+$, required for (M—Cl)$^+$ 284.

Example 21

Preparation of α-phenylacylamino acid methyl ester 19b (R$^9$=Ph, R$^7$=Me)

4-methoxycarbonyl-5-phenyloxazole 18b prepared in EXAMPLE 19 (0.83 g, 4.1 mmol) was dissolved in a mixture of methanol (6 mL) and concentrated hydrochloric acid (2.5 mL) which was stirred at 50° C. for 6 h. The same work-up as described in EXAMPLE 17 gave pure 19b (0.76 g, 81%). m.p. 186°–187° C., $^1$H NMR (DMSO-d$_6$): 3.88 (s, 3 H, OCH$_3$), 6.25 (s, 1 H, CH), 7.61 (m; 2 H, Ar—H$_2$), 7.76 (m, 1 H, Ar—H), and 8.15 (d, 2 H, $^3J_{HH}$=7.5 Hz; Ar—H$_2$), 9.20 (br, 3 H, CH$_3$) Mass (FAB): 194 (M—Cl)$^+$, required for (M—Cl)$^+$ 194.

Example 22

Preparation of bis-2-(3,4-butylenylpyrro)methane 5c (R$^1$R$^2$=CH$_2$CH$_2$CH$_2$CH$_2$)

The dipyrromethane, 5c, may be prepared as follows. To 2-ethoxy carbonyl-3,4-butylenylpyrrol, 1e, (0.42 gram, 2.2 mmol), paraformaldehyde (0.26 gram, 8.6 mmol), is added lithium chloride (0.95 g, 0.014 mmol), water (40 mg, 0.0022 mmol) and DMSO (10 mL). The mixture is de-aerated with argon for 10 minutes and refluxed under argon for 3 hours. The mixture is then poured into ice-H$_2$O (50 g), and extracted with diethylether (2×50 mL). The organic phase is washed with saturated sodium chloride (10 mL) and rotary evaporated in vacuo to give 5c. See page 12.

Example 23

Bis (5-methoxycarbonyl-3,4-diethylpyrro)-(4-trifluoromethylphenyl)methane 4f

A solution of 1b (1.0 g, 5.5 mmol) in CH$_2$Cl$_2$ (15 mL) was de-aerated with argon for 5 min. 4-trifluoromethylbenzaldehyde (1.1 g, 6.3 mmol) and BF$_3$.OEt$_3$ (0.31 g, 2.2 mmol) were added by syringe. After the mixture was stirred at room temperature for 10 h, TLC showed that 1b disappeared and a new component 4f appeared (R$_f$=0.23, CHCl$_3$:hexane=1:1). The volatiles were removed in vacuo at room temperature. The residue was dissolved in ethyl acetate (40 mL) and washed with sodium bicarbonate (50 mL, 5%). The organic layer was separated and the aqueous layer was extracted with ethyl acetate (40 mL). The combined organic phases were concentrated in vacuo. Flash chromatography on silica gel (140×45 mm, CHCl$_3$:hexane=1:1) gave the orange solid product 4f (1.30 g, 90.9%). $^1$H NMR (CDCl$_3$: 0.92 (t, 6 H, CH$_3$, $^3J_{HH}$=7.5 Hz), 1.14 (t, 6 H, CH$_3$, $^3J_{HH}$=7.5 Hz), 2.33 (q, 4 H, CH$_2$, $^3J_{HH}$=7.5 Hz), 2.71 (q, 4 H, CH$_2$, $^3J_{HH}$=7.5 Hz), 3.72 (s, 6 H, OCH$_3$), 5.63 (s, 1 H, CH), 7.18 (d, 2 H, CF$_3$C$_6$H$_4$, $^3J_{HH}$=7.5 Hz), 7.76 (d, 2 H, CF$_3$C$_6$H$_4$, $^3J_{HH}$=8.1 Hz), 8.57 (b, NH, 2 H). $^{13}$C NMR (CDCl$_3$): 15.72 (CH$_3$), 15.78 (CH$_3$), 17.12 (CH$_2$), 18.32 (CH$_2$), 22.00 (CH), 51.05 (OCH$_3$), 117.73, 124.23, 125.82 (q, $^3J_{CF}$=3.1 Hz), 127.50 (q, CF$_3$, $^1J_{CF}$=266.8 Hz), 129.27 (q, $^2J_{CF}$=32.3 Hz), 128.57, 130.73, 134.16, 144.09, 161.79 (C=O). IR (KBr pellet): 594, 778, 1013, 1067, 1091, 1258, 1327, 1410, 1463, 1499, 1654, 1711, 2872, 2933, 2966, 3339 (NH) cm$^{-1}$. HRMS: calcd. 518.23924 for C$_{28}$H$_{33}$F$_3$N$_2$O$_4$, found 518.23978. Elemental analysis: calcd. C, 64.85, H, 6.41, N, 5.40, found C, 64.65, H, 6.20, N, 5.51.

All publications and patent applications in this specification are indicative of the level of ordinary skill in the art to which this invention pertains. All publications and patent applications are herein incorporated by reference to the same extent as if each individual publication or patent application was specifically and individually indicated by reference.

It will be apparent to one of ordinary skill in the art that many changes and modifications can be made in the invention without departing from the spirit or scope of the appended claims.

What is claimed is:

1. A porphyrin compound of the general formula:

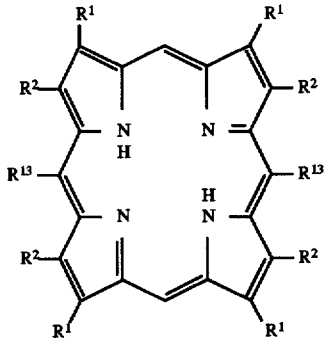

wherein R$^1$ and R$^2$ are each independently C$_1$–C$_{20}$ alkyl, F, Cl, Br, I, NO, NH$_2$, OH, OMe, OEt, SO$_3$H; substituted C$_1$–C$_{20}$ alkyl, C$_1$–C$_{10}$ aryl wherein the substitution includes one or more F, Cl, Br, I, NO$_2$, NH$_2$, OH, OMe, OEt, SO$_3$H groups; and R$^{13}$ is CF$_3$, CH$_2$CF$_3$, CF$_2$CF$_3$, CF$_3$ substituted phenyl at the o, m or p position or a phenyl substituted with one or more F groups.

* * * * *

UNITED STATES PATENT AND TRADEMARK OFFICE
CERTIFICATE OF CORRECTION

PATENT NO. : 5,672,717

DATED : SEPTEMBER 30, 1997

INVENTOR(S) : VERKADE ET AL.

It is certified that error appears in the above-identified patent and that said Letters Patent is hereby corrected as shown below:

Cover page, [75] Inventors: "Jianseng" should read --Jiansheng--

Col. 1, line 13: "5,367,034" should read --5,367,084--

Col. 2, line 12, diagram F: "$R^2$" on right side of diagram should read --"$R^1$"

Col. 2, line 15, diagram F: "$R^1$" on right side of diagram should read --"$R^2$"

Col. 3, line 17: "meso-diphenylporphyfin" should read --meso-diphenylporphyrin--

Col. 5, line 21: "sefines" should read --serines--

Col. 5, line 50, scheme 4: insert -- 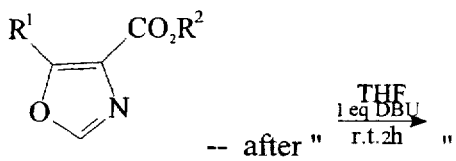 -- after " THF 1 eq DBU r.t. 2h "

Col. 7, line 9: "estefified" should read --esterified--

Col. 9, line 62: "isoeyanoaeetate" should read --isocyanoacetate--

Col. 12, line 42: "isoeyanoacetate" should read --isocyanoacetate--

Col. 18, line 60: "(—$R^1R^2$ —— $CH_2$" should read --$^3J_{PH}$=10.8Hz,--

UNITED STATES PATENT AND TRADEMARK OFFICE
CERTIFICATE OF CORRECTION

PATENT NO. : 5,672,717       PAGE 2 of 5

DATED : SEPTEMBER 30, 1997

INVENTOR(S) : VERKADE ET AL.

It is certified that error appears in the above-identified patent and that said Letters Patent is hereby corrected as shown below:

Col. 20, line 7, scheme C: "↑" should read -- | --

Col. 22, line 28, scheme D: "↑" should read -- | --

Col. 23, line 30: "aidehyde" should read --aldehyde--

Col. 24, line 32: "isocyanoaeetate" should read --isocyanoacetate--

Col. 25, line 18, scheme E: "±99%" should read --≥99%--

Col. 25, line 37, scheme E: "±99%" should read --≥99%--

Col. 26, line 15, scheme E: "↑" should read -- | --

Col. 26, line 18, scheme E: "±98%" should read --≥98%--

Col. 26, line 32, scheme E: "↑" should read -- | --

Col. 26, line 37, scheme E: "±90%" should read --≥90%--

Col. 28, line 10: "Superbase" should read --superbase--

Col. 28, line 32, example 1: insert --$^3J_{ph}$=10.8Hz, -- after the word --$^3J_{PH}$=10.8Hz,--

Col. 28, line 50, example 2: "($R^1=R^3$=Et)" should read --($R^1=R^2=R^3$=Et)--

Col. 28, line 50: "Superbase" should read --superbase--

UNITED STATES PATENT AND TRADEMARK OFFICE
CERTIFICATE OF CORRECTION

PATENT NO. : 5,672,717

DATED : SEPTEMBER 30, 1997

INVENTOR(S) : VERKADE ET AL.

It is certified that error appears in the above-identified patent and that said Letters Patent is hereby corrected as shown below:

Col. 28, line 64: "Superbase" should read --superbase--

Col. 29, line 3: "vaeuo" should read --vacuo--

Col. 29, line 40: "isocyanoaeetate" should read --isocyanoacetate--

Col. 29, line 48: "Superbase" should read --superbase--

Col. 30, line 13: "Superbase" should read --superbase--

Col. 30, line 39: "Superbase" should read --superbase--

Col. 30, line 43: "isocyanoaeetate" should read --isocyanoacetate--

Col. 30, line 65: "Superbase" should read --superbase--

Col. 31, line 13: "-CH)" should read -- -CH$_3$)--

Col. 32, line 31: "$J_{HH}$" should read --$^3J_{HH}$--

Col. 32, line 58: "(g," should read --(q,--

Col. 33, line 32: "THf" should read --THF--

Col. 34, line 30: "CH$_2$" should read --CH$_2$--

UNITED STATES PATENT AND TRADEMARK OFFICE
CERTIFICATE OF CORRECTION

PATENT NO. : 5,672,717

DATED : SEPTEMBER 30, 1997

INVENTOR(S) : VERKADE ET AL.

It is certified that error appears in the above-identified patent and that said Letters Patent is hereby corrected as shown below:

Col. 34, line 39: "LiAlH4" should read --LiAlH$_4$--

Col. 34, line 56: "$^1$HNMR" should read --$^1$H NMR--

Col. 35, line 25: "trimelhoxyphenyl" should read --trimethoxyphenyl--

Col. 35, line 25: "Using the Superbase" should read --using the superbase--

Col. 35, line 28: "Superbase" should read --superbase--

Col. 35, line 59: "Using the Weak Base" should read --using the weak base--

Col. 36, line 14: "Using the Strong Base" should read --using the strong base--

Col. 36, line 15: "R$^7$" should read --R$^6$--

Col. 36, line 22: "hipbasic" should read --biphasic--

Col. 36, line 24: "vaeuo" should read --vacuo--

Col. 36, line 30: "N$_{cq}$" should read --N$_{eq}$--

UNITED STATES PATENT AND TRADEMARK OFFICE
CERTIFICATE OF CORRECTION

PATENT NO. : 5,672,717

DATED : SEPTEMBER 30, 1997

INVENTOR(S) : VERKADE ET AL.

It is certified that error appears in the above-identified patent and that said Letters Patent is hereby corrected as shown below:

Col. 36, line 58: delete second occurrence of "(s, 3 H, $OCH_3$), 3.79"

Col. 38, line 43, claim 1: "$R^{13}$ is $CF_3$, $CH_2CF_3$, $CF_2CF_3$, $CF_3$" should read --$R^{13}$ is $CF_3$, $CH_2$, $CF_3$, $CF_2$, $CH_3$, $CF_2$, $CF_3$, $CF_3$--

Signed and Sealed this

First Day of September, 1998

Attest:

BRUCE LEHMAN

Attesting Officer

Commissioner of Patents and Trademarks